(12) United States Patent
Privitera et al.

(10) Patent No.: US 8,911,085 B2
(45) Date of Patent: Dec. 16, 2014

(54) PUPILARY SCREENING SYSTEM AND METHOD

(75) Inventors: Claudio Privitera, Albany, CA (US); Kamran Siminou, San Clemente, CA (US)

(73) Assignee: Neuroptics, Inc., Irvine, CA (US)

( * ) Notice: Subject to any disclaimer, the term of this patent is extended or adjusted under 35 U.S.C. 154(b) by 0 days.

(21) Appl. No.: 13/543,341

(22) Filed: Jul. 6, 2012

(65) Prior Publication Data

US 2012/0274906 A1    Nov. 1, 2012

Related U.S. Application Data

(63) Continuation of application No. 12/210,185, filed on Sep. 13, 2008.

(60) Provisional application No. 60/972,636, filed on Sep. 14, 2007.

(51) Int. Cl.
| | | |
|---|---|---|
| A61B 3/08 | (2006.01) |
| A61B 3/00 | (2006.01) |
| A61B 3/10 | (2006.01) |
| A61B 3/11 | (2006.01) |

(52) U.S. Cl.
CPC ...................... *A61B 3/112* (2013.01)
USPC ............ 351/202; 351/200; 351/205; 351/221

(58) Field of Classification Search
USPC .......................... 351/200, 202, 205, 221, 246
See application file for complete search history.

(56) References Cited

U.S. PATENT DOCUMENTS

| | | |
|---|---|---|
| 2,445,787 A | 7/1948 | Edgar |
| 3,533,683 A | 10/1970 | Stark et al. |
| 3,533,684 A | 10/1970 | Stark et al. |
| 3,638,640 A | 2/1972 | Shaw |
| 3,903,871 A | 9/1975 | Chisum et al. |
| 3,904,280 A | 9/1975 | Tate, Jr. |
| 3,929,124 A | 12/1975 | Yablonski et al. |
| RE28,873 E | 6/1976 | Morgan |
| 3,966,310 A | 6/1976 | Larson |
| 4,007,980 A | 2/1977 | Bracher et al. |
| 4,157,864 A | 6/1979 | Koller et al. |
| 4,194,815 A | 3/1980 | Trombley |
| 4,410,245 A | 10/1983 | Koester |
| 4,485,820 A | 12/1984 | Flower |

(Continued)

FOREIGN PATENT DOCUMENTS

| | | |
|---|---|---|
| JP | 7171104 | 7/1995 |
| JP | 8140936 | 6/1996 |

(Continued)

OTHER PUBLICATIONS

AMTech GmbH, "Introducing CIP: compact integrated pupillograph and nystagmograph", 18 pages (1997).

(Continued)

*Primary Examiner* — Dawayne A Pinkney
(74) *Attorney, Agent, or Firm* — Hybrid Law Group P.C.

(57) ABSTRACT

A method of screening a pupil of a subject to determine whether the pupil reflex resembles a canonical pupil reflex is disclosed. The method comprises the steps of stimulating the pupil with a stimulus source, such as a pupilometer and determining whether one of various pupillary response conditions is met.

5 Claims, 17 Drawing Sheets

(56) References Cited

U.S. PATENT DOCUMENTS

| | | | |
|---|---|---|---|
| 4,641,349 | A | 2/1987 | Flom et al. |
| 4,649,908 | A | 3/1987 | Ghaly |
| 4,652,099 | A | 3/1987 | Lichtman |
| 4,664,490 | A | 5/1987 | Rol |
| 4,755,043 | A | 7/1988 | Carter |
| 4,863,260 | A | 9/1989 | Gersten et al. |
| 4,871,247 | A | 10/1989 | Haynes |
| 4,907,597 | A | 3/1990 | Chamoun |
| 4,907,872 | A | 3/1990 | Schirmer et al. |
| 4,966,452 | A | 10/1990 | Shields et al. |
| 5,010,891 | A | 4/1991 | Chamoun |
| 5,022,749 | A | 6/1991 | Ogura |
| 5,061,279 | A | 10/1991 | Friel |
| 5,117,835 | A | 6/1992 | Mick |
| 5,137,345 | A | 8/1992 | Waldorf et al. |
| 5,139,326 | A | 8/1992 | Snider |
| 5,179,953 | A | 1/1993 | Kursar |
| 5,187,506 | A | 2/1993 | Carter |
| 5,200,773 | A | 4/1993 | Volk |
| 5,204,703 | A | 4/1993 | Hutchinson |
| 5,214,456 | A | 5/1993 | Gersten |
| 5,231,674 | A | 7/1993 | Cleveland et al. |
| 5,291,560 | A | 3/1994 | Daugman |
| 5,297,554 | A | 3/1994 | Glynn et al. |
| 5,336,215 | A | 8/1994 | Hsueh |
| 5,387,952 | A | 2/1995 | Byer |
| 5,408,359 | A | 4/1995 | Ferrett et al. |
| 5,408,998 | A | 4/1995 | Mersch |
| 5,430,505 | A | 7/1995 | Katz |
| 5,490,098 | A | 2/1996 | Kardon |
| 5,528,323 | A | 6/1996 | Fujieda et al. |
| 5,543,865 | A | 8/1996 | Nanjo |
| 5,565,939 | A | 10/1996 | Fujieda |
| 5,608,472 | A | 3/1997 | Szirth et al. |
| 5,617,872 | A | 4/1997 | Scinto et al. |
| 5,646,709 | A | 7/1997 | Carter |
| 5,649,727 | A | 7/1997 | St. Louis |
| 5,661,538 | A | 8/1997 | Carter |
| 5,684,562 | A | 11/1997 | Fujieda |
| 5,772,298 | A | 6/1998 | Miyake |
| 5,784,145 | A | 7/1998 | Ghodse et al. |
| 5,813,982 | A | 9/1998 | Baratta |
| 5,831,667 | A | 11/1998 | Siminou |
| 5,841,502 | A | 11/1998 | Miwa |
| 5,883,691 | A | 3/1999 | Ishikawa et al. |
| 5,892,568 | A | 4/1999 | Carter |
| 5,903,333 | A | 5/1999 | Siminou et al. |
| 5,953,097 | A | 9/1999 | Stark |
| 5,963,300 | A | 10/1999 | Horwitz |
| 6,022,109 | A * | 2/2000 | Dal Santo ............... 351/221 |
| 6,115,111 | A | 9/2000 | Korah et al. |
| 6,116,736 | A | 9/2000 | Stark et al. |
| 6,199,985 | B1 | 3/2001 | Anderson |
| 6,260,968 | B1 | 7/2001 | Stark et al. |
| 6,389,169 | B1 | 5/2002 | Stark et al. |
| 6,637,881 | B1 | 10/2003 | Siminou |
| 6,820,979 | B1 | 11/2004 | Stark et al. |
| 7,147,327 | B2 | 12/2006 | Stark et al. |
| 7,216,985 | B2 | 5/2007 | Siminou et al. |
| 7,334,895 | B2 | 2/2008 | Kandel et al. |
| 7,670,002 | B2 | 3/2010 | Stark et al. |
| 7,789,510 | B2 | 9/2010 | Fateh |
| 2002/0099305 | A1 | 7/2002 | Fukushima et al. |
| 2002/0181786 | A1 | 12/2002 | Stark et al. |
| 2004/0246441 | A1 * | 12/2004 | Stark et al. ............... 351/205 |
| 2005/0165327 | A1 | 7/2005 | Thibault et al. |
| 2005/0200808 | A1 | 9/2005 | Wyatt |
| 2006/0030760 | A1 | 2/2006 | Geiger |
| 2009/0306538 | A1 | 12/2009 | Siminou |
| 2010/0195049 | A1 | 8/2010 | Stark et al. |

FOREIGN PATENT DOCUMENTS

| | | |
|---|---|---|
| JP | 10500032 | 1/1998 |
| WO | WO 95/22278 | 9/1995 |
| WO | WO 96/03070 | 2/1996 |
| WO | WO 00/64330 | 11/2000 |
| WO | WO 02/46801 | 6/2002 |

OTHER PUBLICATIONS

Andrews et al. "Functional recovery after traumatic transtentorial herniation" Neurosurgery 29(2):227-231 (1991).

Asano et al., "Pupillometry", Quarterly progress report No. 66, Mass. Inst. of Technology, 402-412 (Jul. 15, 1962).

ASL Applied Science Laboratories, "Pupilscreen, pupilscreeen automatic self measurement pupillometry", 5 pages.

ASL, Model 1050, "Pupilscan and pupilscreen" 5 pages (1997).

Bishop, "Pathologic pupillary signs: self-learning module, part 1," Critical care nurse 11(6):56-63.

Bishop, "Pathologic pupillary signs: self-learning module, part 2," Critical care nurse 11(7):58-67.

Bishop, "Pathologic pupillary signs: self-learning module, part 3," Critical care nurse 11(8):30-32.

Blackmon et al., "Model-based supervisory control in telerobotics," Presence Teleoper Virtual Environ 5(2): 205-23 (1996).

Braakman et al. Systematic selection of prognostic features in patients with severe head injury Neurosurgery 6(4): 362-70 (1980).

Chesnut et al. "The localizing value of asymmetry in pupillary size in severe head injury: relation to lesion type and location" Neurosurgery 34(5): 840-5 (1994).

Choi et al. "Enhanced specificity of prognosis in severe head injury" J. Neurosurg 69(3):381-5 (1988).

Choi et al., "String editing analysis of human visual search," Optom Vis Sci. 72(7): 439-51 (1995).

Clusmann et al. "Fixed and dilated pupils after trauma, stroke and previous intracranial surgery: management and outcome" J. Neurol. Neurosurg Psychiatry 71(2):175-81 (2001).

Du et al. "Evaluation of the portable infrared pupillometer" Neurosurgery 57(1):198-203 (2005).

Fairville Medical Options, Inc., "Pupilscan II: hand-held, cordless pupillometer", 4 pages (Feb. 12, 1997).

Fairville Medical Options, Inc., "Pupilscan II: hand-held, electric pupillometer", 3 pages.

Finnila C.A., "A convenient eye position and pupil size meter" (partial), 4 pages (1960).

Gauthier et al., "Adapted head-and eye-movement responses to added-head inertia," Aviat Space Environ Med. 57(4): 336-42 (1986).

Goebert "Head injury associated with a dilated pupil" Surg Clin North Am 50(2):427-432 (1970).

Hung et al., "The interpretation of kernels—an overview," Ann Biomed Eng. 19(4): 509-19 (1991).

Krenz, et al., Neurophysiological Model of the Normal and Abnormal Human Pupil, IEEE Transactions on Biomedical Engineering, vol. BME-32, No. 10, pp. 817-825, Oct. 1985.

Krieger et al., "Prognostic and clinical relevence of puillary responses, intracdanial pressure monitoring, and brainstem auditory evoked potentials in comatose patients with acute supratentorial mass lesions", critical care medicine, 21:1944-1950 (Dec. 1993).

Levin et al. "Neurobehavioral outcome 1 year after severe head injury. Experience of the traumatic coma data bank" J. Neurosurg. 73(5):699-709 (1990).

Litvan et al. "Pupillary diameter assessment: need for a graded scale" Neurology 54(2):530-1 (2000).

Manley et al. "Infrared pupillometry during uncal herniation" J. Neurosurg Anesthesiol 14(3):223-8 (2002).

Marmarou et al. "Prognostic value of the Glasgow coma scale and pupil reactivity in traumatic brain injury assessed pre-hospital and on enrollment: an Impact analysis" J. Neurotrauma 24(2):270-80 (2007).

Marshal et al., "Pupillary abnormalities, elevated intracranial pressure and mass lesion location", Intracranial pressure VI, Springer-Verlag Berlin Heidelberg, 656-660 (1986).

(56) References Cited

OTHER PUBLICATIONS

Marshall et al. "The outcome of severe closed head injury" J. Neurosurg 75:S28, (1991).
Marshall et al., The oval pupil: clinical significance and relationship to intracranial hypertension, J. Neurosurg, 58:566-568 (Apr. 1983).
Meeker et al. "Pupil examination: validity and clinical utility of an automated pupillometer" J. Neurosci Nurs. 37(1):34-40 (2005).
Miyao et al., "Effects of VDT resolution on visual fatigue and readability: an eye movement approach," Ergonomics 32(6): 603-14 (1989).
Myers et al. "level dependent signal flow in the light pupil reflex" Biological Cybernetics, 68:229-234 (1993).
Myers et al., "Level dependent signal flow in the light pupil reflex. II. Phase velocity of responses to sinusoidal light stimuli," Biol Cybern. 68(3): 235-40 (1993).
Narayan et al. "Improved confidence of outcome prediction in severe head injury: a comparative analysis of the clinical examination, multimodality evoked potentials, CT scanning, and intracranial pressure" J. Neurosurg. 54(6): 751-62 (1981).
Nguyen et al., "Model control of image processing: pupillometry," Comput Med Imaging Graph. 17(1): 21-33 (1993).
Ritter et al "Brain stem blood flow, pupillary response and outcome in patients with severe head injuries" Neurosurgery 44(5):941-8 (1999).
Sakas et al. "One-year outcome following craniotomy for traumatic hematoma in patients with fixed dilated pupils" J. Neurosurg 82(6):961-5 (1995).
Stark et al., "Instrumentation and robotic image processing using top-down model control", Robotics and manufacturing, ASME press:675-682 (1988).
Stark et al., "Pupil Unrest: An example of noise in a biological servomechanism", Nature, 4639, 857-858 (Sep. 27, 1958).
Stark et al., "Top-down and bottom-up image processing", Proceedings of IEEE 1997 international conference on neural networks, 6 pages (Jun. 1997).
Stark, L., "Stability oscillations and noise in the human pupil servomechanism", Proceedings of the IRE, 1925-1939 (1959).
Stark, L., "The pupil as a paradigm example a neurological control system: mathematical approaches in biology", The pupil: anatomy, physiology, and clinical applications, vol. I, Iowa State University Press:630-647 (1993).
Stark, The Pupil as a Paradigm for Neurological Control Systems, IEEE Transactions on Biomedical Engineering, vol. BME-31, No. 12, pp. 919-923, Dec. 1984.
Sun et al., "A systems model for the pupil size effect. I. Transient data," Biol Cybem. 48(2):101-8 (1983).
Sun et al., "Comparative patterns of reading eye movements in Chinese and English," Percept Psychophys. 37(6): 502-6 (1985).
Taylor et al. "Quantitative pupillometry, a new technology: normative data and preliminary observations in patients with acute head injury. Technical note." J. Neurosurg. 98(1):205-213 (2003).
Usui et al., "Sensory and motor mechanisms interact to control amplitude of pupil noise", Vision Res., 18:505-507 (1978).
Wilson et al. "Determining interrater reliability of nurses' assessments of pupillary size and reaction" J. Neurosci. Nurs. 20(3):189-92 (1988).
Worthley "The pupillary light reflex in the critically ill patient" Crit Care Resusc 2(1):7-8 (2000).
Wyatt, Harry J., "The Form of the Human Pupil", Vision Res., vol. 35, No. 14, pp. 2021-2036, Pergamon 1995.
Yarbus A., "Eye movements and vision", Plenum Press, N.Y. 28-41 (1967).
Zhou et al., "Efficiency of search patterns," Comput Biol Med. 23(6): 511-24 (1993).

\* cited by examiner

PUPILARY SCREENING SYSTEM AND METHOD

RELATED APPLICATIONS

This is a continuation of U.S. application Ser. No. 12/210,185, filed Sep. 13, 2008, which claims priority from U.S. Provisional Patent Application Ser. No. 60/972,636, filed Sep. 14, 2007. The entirety of each of the foregoing patent applications is incorporated herein by reference.

FIELD OF THE INVENTION

The present invention relates generally to pupilometry systems and, more particularly, to pupilometry systems having a pupil irregularity detection, pupil tracking, and pupil response detection capability, as well as glaucoma screening capability, corneal topography measurement capability, intracranial pressure detection capability, and ocular aberration measurement capability. In one particularly innovative aspect, the present invention relates to hand-held pupilometry systems having a pupil irregularity detection capability, to methods and processing sequences used within such systems, and to methods of using such systems.

In another innovative aspect, the present invention relates to a medical diagnostics system incorporating a pupilometer and medical database for correlating actual or derived pupilary image analysis data with stored medical data to formulate medical diagnoses, and to methods of implementing and utilizing such a diagnostics system.

In another innovative aspect, the present invention relates to a medical diagnostics system incorporating a pupilometer which can be used to screen for Glaucoma, and for methods of implementing and utilizing such a diagnostics system.

In another innovative aspect, the present invention relates to a medical diagnostics system incorporating a pupilometer for detecting elevated intracranial pressure, and for methods of implementing and utilizing such a diagnostics system.

In another innovative aspect, the present invention relates to a medical diagnostics system incorporating a pupilometer for assessing the level of brain function, and for methods of implementing and utilizing such a diagnostics system.

In another innovative aspect, the present invention relates to a medical diagnostics system incorporating a pupilometer for testing the functional integrity of afferent peripheral and cranial pathways as well as testing efferent cranial nerve involvement in patients with afferent pupilary defects, and for methods of implementing and utilizing such a diagnostics system.

In another innovative aspect, the present invention relates to a medical diagnostics system incorporating a pupilometer for testing the functional integrity of auditory pathways, and for methods of implementing and utilizing such a diagnostics system.

BACKGROUND OF THE INVENTION

Systems for monitoring pupil size and pupil responsiveness characteristics are well known in the art and are generally referred to as pupilometry systems or, simply, pupilometers. One early pupilometer is described in U.S. Pat. No. 3,533,683, which issued to Stark et al. on Oct. 13, 1970 and is entitled "Dynamic Pupilometers Using Television Camera System" (incorporated herein by reference). The Stark et al. system employed a television camera system, a digital computer system, an infrared light source, and a visual light stimulator for determining the instantaneous size of a pupil as an eye (or neurologic pupilary control system) of a patient was exposed to various stimuli. Like the early Stark et al. system, conventional pupilometers measure, for example, the diameter of a pupil before and after the pupil is exposed to a light stimulus pulse and also measure the rates at which the pupil may constrict and dilate in response to the initiation and termination of the light stimulus pulse. Pupilometers may comprise hand-held units or, alternatively, may comprise desk or table-mounted, stand-alone units. Pupilometers also generally include some mechanism for ensuring that an imager within the pupilometer is properly positioned in relation to a pupil to be imaged. For example, U.S. Pat. No. 5,646,709 (incorporated herein by reference), issued to Elbert P. Carter, describes an electronic centering system for ensuring that a pupilometer is properly positioned in relation to a pupil to be imaged. Similarly, U.S. Pat. No. 5,187,506 (incorporated herein by reference), issued to Elbert P. Carter, describes an eye orbit housing for ensuring proper positioning between a pupilometer and an eye of a subject prior to the initiation of a pupilary scanning procedure.

Those skilled in the art will appreciate, however, that for a pupilometer to have maximum utility maximum flexibility should be provided for positioning the imager. For example, in the case of a hand-held system few, if any, restrictions should be placed upon the orientation of the imager prior to enabling an imaging function. The reason for this is that medical personnel at, for example, an accident site may have difficulty in positioning an imager in a prescribed position for acquiring pupilary response data. Thus, it is believed that, for hand-held units in particular, a need exists within the pupilometer field for improved data acquisition and processing systems and methods, as such systems and methods may substantially reduce system dependence on imager orientation and may allow pupilometers to become more user friendly.

Similarly, those skilled in the art will appreciate that a need exists for pupilometers that are capable of evaluating more than a mere pupilary response to light stimulus pulses. For example, it is believed that a substantial need exists for a pupilometer that is capable not only of measuring changes in pupilary diameter in response to one or more light stimulus pulses, but also of evaluating pupil shape and/or segmental responses to a visual stimulus. Stated somewhat differently, it is believed that a substantial need exists for a pupilometer having a pupilary shape irregularity or non-uniformity detection capability.

Finally, it is believed that a substantial need exists for pupilometer-based diagnostics systems, as such systems may provide medical practitioners with a cost effective, non-invasive means for gathering and assessing numerous physiologic parameters.

For example, the present invention can be used to screen for Glaucoma, which is the second leading cause of blindness in the world. Visual field perimetry is presently used for diagnosing Glaucoma. In visual field perimetry, a white background and multiple green flicker sources are used. The green sources are randomly turned on for approximately one second durations and the subject patient is asked to press a button if he/she sees a green light. The procedure is repeated until the entire visual field is mapped for each eye. Loss of visual field sensitivity is indicative of Glaucoma.

The current standard of care for Glaucoma detection, however, suffers form inaccuracy and human/patient error. The current standard of care relies on the patient to respond to his or her visual detection of green light by pressing a button. The patient has a limited window of time in which to respond to the green light. Thus, if the patient is not concentrating or responds too quickly or too slowly, the perimetry device will not register the patient's response, and the accuracy of the diagnosis is compromised. Furthermore, current perimetry devices are large machines that are immobile. They are for use in doctors' offices only. Thus, a need exists for improved systems and methods for Glaucoma detection, and the present invention meets these needs and solves the problems associated with standard techniques.

Another area of diagnostic need relates to assessing the level of brain function to diagnose disorders such as autism, age-related disorders, and drug impairment or intoxication. Neurological exams today do not typically include pupilometry beyond the use of a pin-light. Currently, expensive and/or time-consuming tests are required to diagnose impairment of brain function. And, the pin-light test is subjective, non-quantifiable, and inaccurate. The present invention solves these by providing a method and system to closely track the pupil while presenting the eye with a moving visual stimuli to determine the level of coordination. The present invention is capable of quantifying tracking errors, which might occur in the course of a neurological exam, and reduces the subjectivity and increases the repeatability of exams to assess brain function.

Another area of diagnostic need is diagnosis of neurological disease or trauma. Dermatome mapping of patients is commonly done with a pin-prick to determine the level of dorsal root or spinal cord injury. This test, however, is subjective and usually requires cognitive response from a patient. There exists a need for noninvasive diagnosis of neural damage or trauma. The present invention fills that need by providing a means of quantitatively measuring pupilary response to noxious stimulation. Furthermore, this invention is useful in diagnosing dorsal root and spinal cord injuries in unconscious patients with no cognitive response capabilities. It is further useful in diagnosing and monitoring the progression of demyelinating diseases such as multiple sclerosis, which affects conduction velocity through nerve fibers. In addition, testing the level of epidural anesthetic block may be accomplished using pupilometry with this automated stimulus control.

Finally, an area of diagnostic need relates to testing the functional integrity of auditory pathways, i.e., hearing screening. Particularly with infants, hearing has been subjectively screened using stimuli such as in a clap test while observing the startle response. Other tests, such as EEG-type brain stem audible evoked potential (AEP) monitoring systems have been used, but require attachment of electrodes to the scalp and are cumbersome to use. Middle ear tone-feedback monitoring is also used, but is not capable of measuring latency information. The present invention solves these and other problems associated with the prior art by providing hearing screening using objective pupilometer-based testing systems and methods. The pupilometer-based systems are not cumbersome, are easy to use and provide latency information for diagnosing and monitoring the progression of demyelinating diseases.

SUMMARY OF THE INVENTION

In one particularly innovative aspect, a method of screening a pupil of a subject to determine whether the pupil reflex resembles a canonical pupil reflex. The method comprises the steps of stimulating the pupil with a stimulus source is disclosed. The method further includes the steps of using a pupilometer to track the pupil's constriction response over a duration of time, wherein the step of tracking the pupil constriction response begins substantially simultaneously with or immediately subsequent to time 0 and lasts for a period of time y, and using the pupilometer to collect a plurality of data points in which each data point corresponds with a diameter of the pupil at a specific time within the time duration y. The method further includes the step of generating a pupil data profile by compiling the data points and determining whether one or more conditions are met, wherein the one or more conditions comprises the following: (a) more than two data points exist representing the same pupil diameter at three or more separate times during duration y; (b) a first phase of the pupilary reflex response exists, wherein said first phase is characterized by a period of non-constriction immediately subsequent to time 0, said first phase having a duration of less than about 100 msec or greater than about 1000 msec; (c) two data points exist representing the same pupil diameter at two separate times $y^1$ and $y^2$ during duration y, wherein the duration of time between $y^1$ and $y^2$ is less than about 100 msec; or (d) during the first phase of the pupilary reflex, the diameter of the pupil increases before it decreases. Existence of one of said conditions indicates that the pupil reflex does not resemble a canonical reflex.

In another innovative aspect, another method of screening a pupil of a subject to determine whether the pupil reflex resembles a canonical pupil reflex is disclosed. The method comprises the steps of stimulating the pupil with a stimulus source is disclosed. The method further includes the steps of using a pupilometer to track the pupil's constriction response over a duration of time, wherein the step of tracking the pupil constriction response begins substantially simultaneously with or immediately subsequent to time 0 and lasts for a period of time y, and using the pupilometer to collect a plurality of data points in which each data point corresponds with a diameter of the pupil at a specific time within the time duration y. The method further includes the step of generating a pupil data profile by compiling the data points and determining whether the following four conditions are met: (a) no more than two data points exist representing the same pupil diameter at separate times during duration y; (b) a first phase of the pupilary reflex response exists, wherein said first phase is characterized by a period of non-constriction immediately subsequent to time 0, said first phase having a duration of greater than about 100 msec and less than about 1000 msec; (c) if two data points exist representing the same pupil diameter at two separate times $y^1$ and $y^2$ during duration y, then the duration of time between $y^1$ and $y^2$ is greater than about 100 msec; and (d) during the first phase of the pupilary reflex, the diameter of the pupil does not increase before it decreases. The absence of one of the four conditions indicates that the pupil reflex does not resemble a canonical reflex.

Other objects and features of the present invention will become apparent from consideration of the following description taken in conjunction with the accompanying drawings.

DESCRIPTION OF PREFERRED EMBODIMENTS

Figure 1:
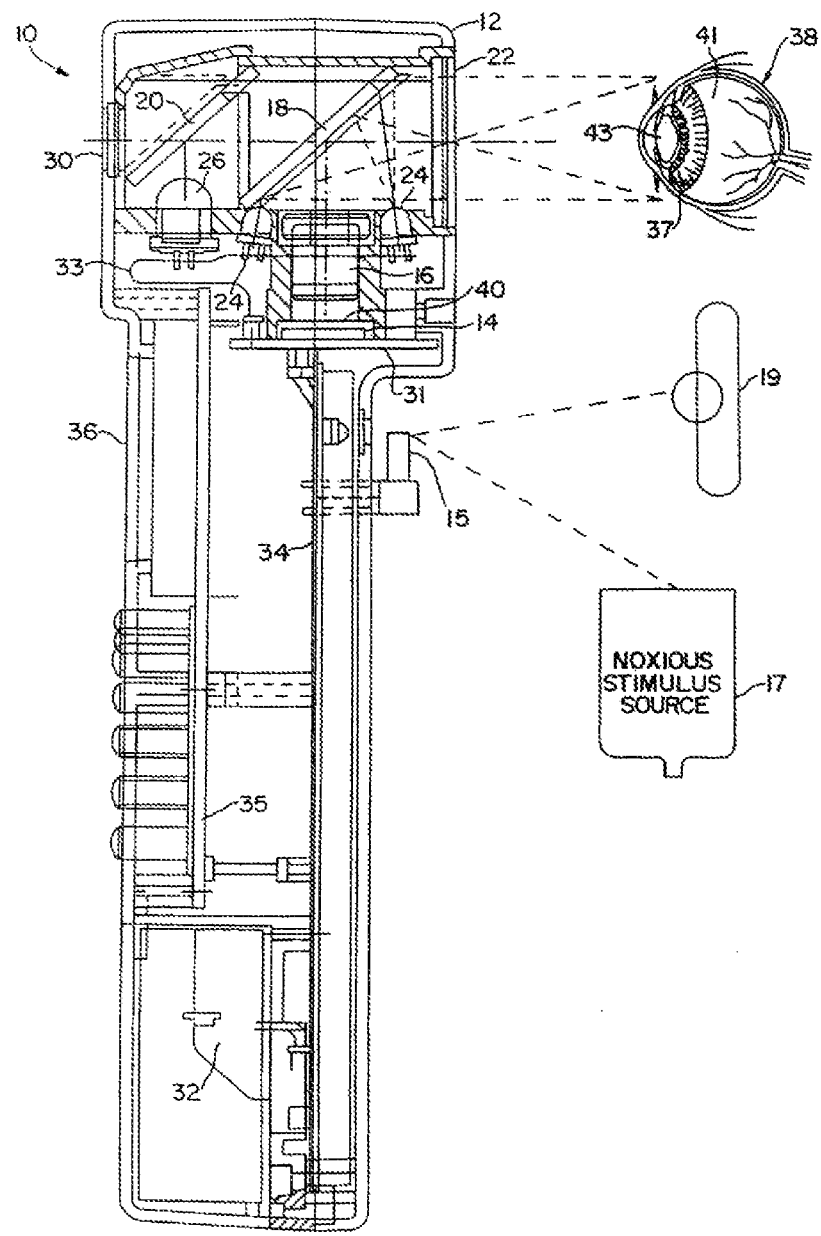
FIG. 1 is a cross-sectional view of a hand-held pupilometer in accordance with a preferred form of the present invention.
Figure 2:
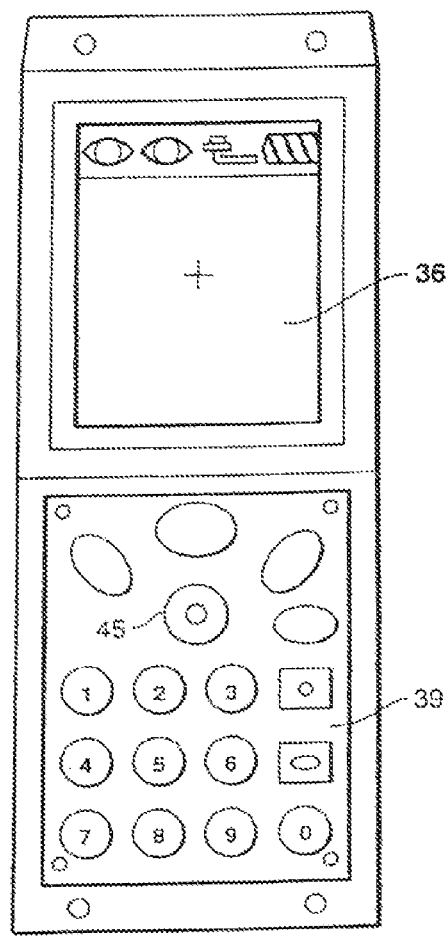
FIG. 2 is an illustration of a liquid crystal display and keypad that may be provided on a hand-held pupilometer in accordance with the present invention.

A. Hardware Components of a Pupilometer in Accordance with the Present Invention Turning now to the drawings, FIG. 1 provides a cross-sectional view of a hand-held pupilometer 10 in accordance with the present invention. FIG. 2 provides an illustration of a liquid crystal display and key pad that may be provided on the hand-held pupilometer 10, and FIG. 3 is an enlarged cross-sectional view of an imaging section of the hand-held pupilometer 10.

Figure 3:
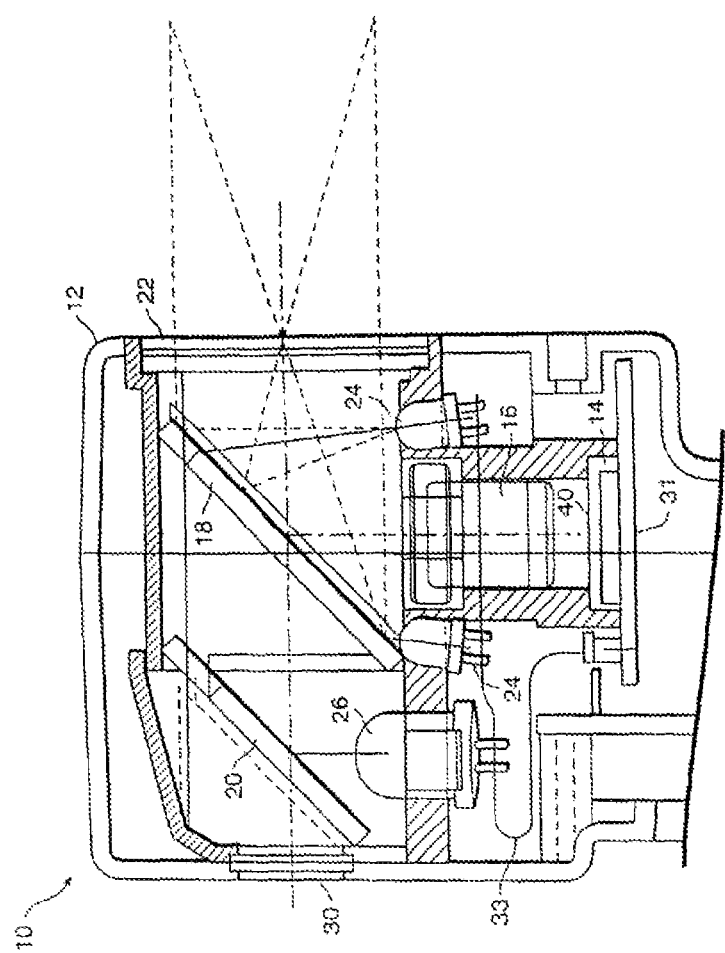
FIG. 3 is an enlarged cross-sectional view of an imaging section of a hand-held pupilometer in accordance with the present invention.

As shown in FIGS. 1-3, the pupilometer 10 preferably includes a housing 12 wherein an imaging sensor 14, an objective lens 16, first and second beam splitters 18 and 20, a shield 22, four infrared (IR) LEDs 24, two yellow LEDs 26, a blue LED 28 (shown in FIG. 4), a reticle 30, a battery 32, an image signal processing board 34 and a liquid crystal display 36 are mounted. Stated somewhat differently, the pupilometer may comprise a viewing port (reticle 30 and shield 22), an imaging system (objective lens 16, imaging sensor 14 and related image processing electronics), an illumination system (IR LEDs 24, blue LED 28 and related control circuitry) and a stimulus system (yellow LEDs 26 and related control circuitry).

Figure 10:
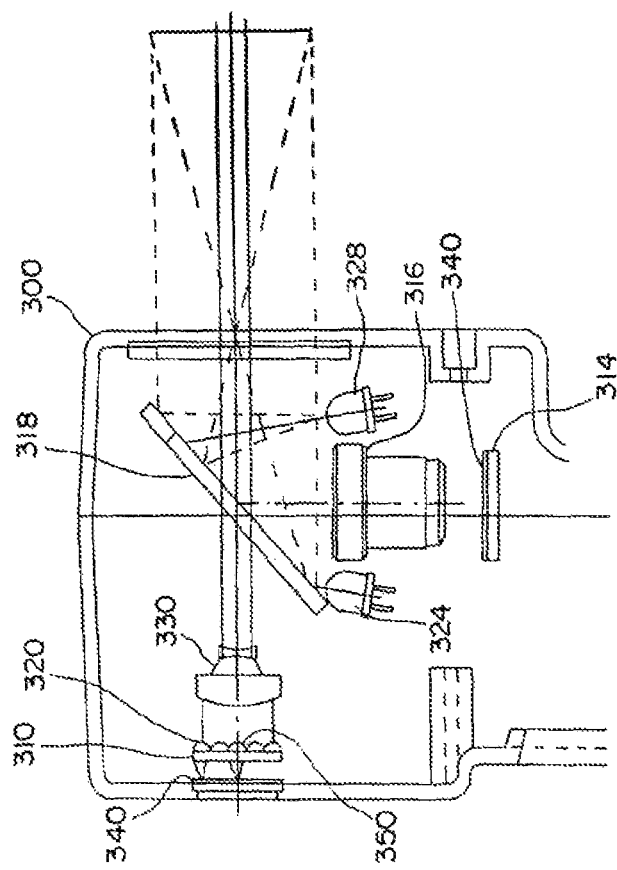
FIG. 10 is a cross-sectional view of a hand-held pupilometer in accordance with yet another embodiment of the present invention.
Figure 13:
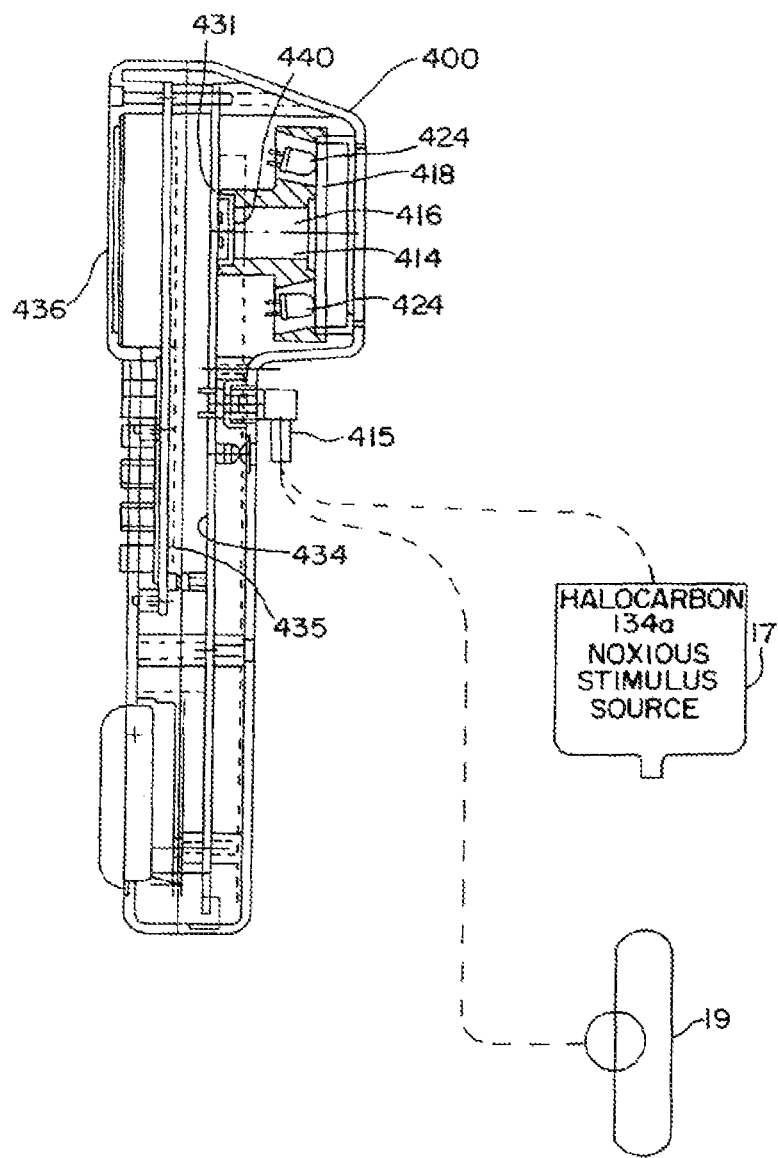
FIG. 13 is a cross-sectional view of a direct-view hand-held pupilometer in accordance with another embodiment of the present invention.

Other embodiments that include some or all of the aforementioned elements are shown in FIGS. 10 and 13. In FIG. 10, the pupilometer 300 further includes a lenslet array 330, and a diode array 340. In FIG. 13, the pupilometer 400 has all of the components of the pupilometer 10, except that it does not have beam splitters, a viewing reticle, blue LEDS, or yellow LEDS. It does, however, contain white LEDS, now shown, a filter glass 418, and an auxiliary connector 415.

1. The Viewing Port

The viewing port (reticle 30 and shield 22) is provided to aid a user in properly positioning the pupilometer 10 for initial data acquisition. By looking through the reticle 30 and shield 22, the user of the pupilometer 10 is able to properly position the pupilometer 10 in front of an eye 38 of a patient, such that an image of the pupil of the patient's eye may be projected onto the imaging sensor 14. The reticle 30 preferably has circular targets (not shown) silk screened or etched on one surface. The targets are positioned along the user's line of sight so as to appear concentric with the iris and pupil of an eye 38 under observation.

Those skilled in the art will appreciate that the reticle 30 and shield 22 also serve as environmental barriers and function to minimize exposure of the imaging system to caustic cleaning agents, biological material and airborne dust, all of which can have a negative impact upon the performance of the imaging system.

Pupilometers 300 and 400, as shown in FIGS. 10 and 13 respectively, do not contain a viewing port as described in connection with pupilometer 10. In pupilometers 300 and 400, the reticle and viewing port have been replaced by functions of the LCD. For example, in FIG. 13, the LCD 436 provides a low frame rate image of the eye during the targeting procedure with graphical indications that the software has detected the iris and pupil. The frame rate can be 6 frames per second, more preferably 10 frames per second, more preferably 25 frames per second, more preferably 50 frames per second, more preferably 100 frames per second, more preferably 200 frames per second, and most preferably 500 frames per second.

An electronic window, which helps the user center the subject's eye, is also provided during the targeting phase. In the process of targeting, an image of the eye is displayed on the LCD 436. Graphical aids, such as black lines or boxes are displayed to help position the device over the eye. The image on the LCD is updated at a rate of about 6 frames per second, more preferably 10 frames per second, more preferably 25 frames per second, more preferably 50 frames per second, more preferably 100 frames per second, more preferably 200 frames per second, and most preferably 500 frames per second.

The LCD 436 can be monochromatic or color. A color LCD 436 can improve the targeting process by providing graphical feedback about the quality of the tracking/imaging in a different color than that represented by the eye.

2. The Imaging System

The imaging sensor 14 preferably comprises a N×M bit CMOS imaging sensor of a type that is commercially available. One such imaging sensor is the 384×288 bit, Model OV5017, CMOS imaging sensor manufactured and distributed by Omnivision Technologies, Inc. of Sunnyvale, Calif. The imaging sensor 14 is mounted to an imager board 31 of the pupilometer 10 and is coupled to a microprocessor (not shown) provided on a main processing or mother board 34 of the pupilometer 10. This allows for direct capture of digital images. Images in the form of 8 bit (or greater) gray scale bit maps are stored in system memory for image analysis and display on the liquid crystal display 36 (shown in FIG. 2). The microprocessor (not shown) preferably comprises an Elan SC 400 manufactured and distributed by Advanced Micro Devices, Inc., of Austin, Tex.

The imaging system of the present invention is designed such that, when the hand-held pupilometer 10 is positioned in front of the eye 38 of a subject, a properly illuminated and in-focus image of the pupil 43 of the subject's eye 38 is obtained at the sensor plane 40 of the pupilometer 10. The objective lens 16 and a first beam splitter (i.e., wavelength selective filter) 18 preferably are used to focus an image of the pupil 43 of the subject's eye 38 on the sensor plane 40. In a preferred form, the objective lens 16 comprises a five element lens having a focal length of 7.0 mm. The first beam splitter 18 preferably comprises a glass substrate having a thickness of 1.6 mm that is coated with a multi-layer dielectric coating (not shown) to form a wavelength selective filter. The subject side 42 of the beam splitter 18 is coated to enhance reflection at the blue and infrared (IR) wavelength bands with a 45° angle of incidence. The user side 44 of the beam splitter 18 is AR coated to minimize effects resulting from multiple reflections in the image path.

Thus, as shown in FIGS. 1 and 3, the beam splitter 18 functions to direct blue and/or IR light generated by the blue and IR LEDs 28 and 24, respectively, toward the eye 38 of a patient and to provide a return path to the imaging sensor 14 for blue and/or IR light that is reflected from the eye 38 of the patient.

The microprocessor (not shown) provided on the main signal processing board 34 controls the operation and function of the various components comprising the imaging system as described more fully below.

The imaging system of the pupilometer 300 shown in FIG. 10 is similar to that described with respect to pupilometer 10. The beam splitter 318, imaging sensor 314 including imaging plane 340, and objective lens 316, each can be of the same type as beam splitter 18, imaging sensor 40 including imaging plane 14, and objective lens 16 respectively. The objective lens 316 and beam splitter 318 are used to focus an image of the pupil of the subject's eye on the sensor plane 340.

Pupilometer 400, as shown in FIG. 13, functions in the same manner except that a beam splitter is not needed to direct an image of the pupil of the subject's eye on the sensor plane 440. Light passes through filter glass 418 and objective lens 416, which together focus an image of the pupil on sensor plane 440. The sensor plane 440 is part of the imaging sensor 414. Furthermore, the filter glass 418 is in direct contact with and mounted on the objective lens 416. The filter glass 418 can remove all spectral components except for IR light. It can also improve the image contrast at the sensor and reduce variation in ambient light conditions, which can also affect performance.

Thus, as shown in FIG. 10, the beam splitter 318 functions to direct blue and/or IR light generated by the blue and IR LEDS, 328 and 324 respectively, toward the eye of a patient, and to provide a return path to the imaging sensor 314 for blue and/or IR light that is reflected from the eye of the patient.

3. The Illumination System

With respect to pupilometers 10, 300, and 400, the illumination system preferably comprises a blue light emitting diode (LED) 28 and 328 respectively (not shown with pupilometer 400 in FIG. 13), and four infrared (IR) LEDs 24, 324, and 424 respectively. Although not shown in pupilometer 400, it too can include a blue LED mounted in the same manner as in pupilometers 10 and 300. The IR LEDs 24, 324, and 424 preferably are arranged symmetrically about the objective lens 16, 316, and 416 respectively. The IR LEDs 24 and blue LED 28 are coupled to a flex circuit 33 that is coupled to the main signal processing board 34 of pupilometer 10. Although not shown in FIGS. 10 and 13, the same is true for pupilometers 300 and 400. When activated by the microprocessor (not shown), the IR LED's 24 emit IR light preferably having a wavelength of substantially 850 nm. Again, this is also true with respect to the IR LEDS in pupilometers 300 and 400. Thus, those skilled in the art will appreciate that the emission bandwidth of the IR LEDs lies beyond the physiological response of the human eye but within the photoelectric response of the imaging sensors 14, 314, and 414. Stated somewhat differently, while the human eye is unable to detect the IR light emitted by the IR LEDs, IR light generated by the IR LEDs and reflected by the eye 38 of a subject may be detected by the imaging sensors.

Figure 4:
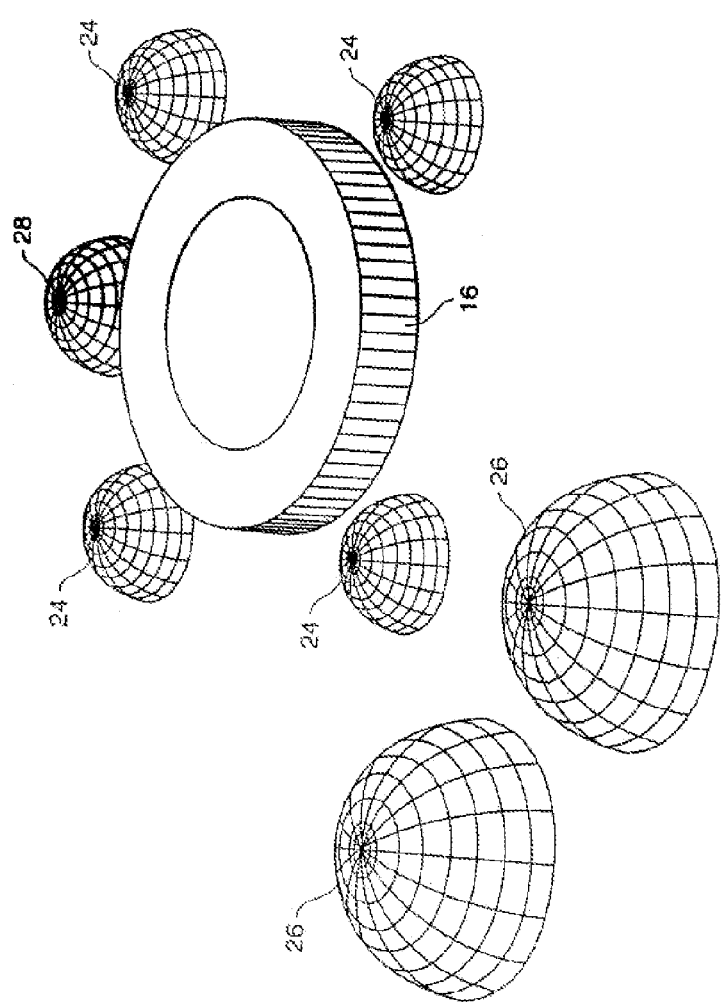
FIG. 4 is a three-dimensional plan view showing a preferred arrangement of a plurality of IR, blue and yellow LEDs that may be used for ocular illumination and stimulation within a pupilometer in accordance with the present invention.

The four IR LEDs 24, 324, and 424 in each of pupilometers 10, 300, and 400 respectively, preferably are arranged in diametrically opposed groups of two, as shown in FIG. 4. By arranging the IR LEDs in the manner shown in FIG. 4, it is possible to more precisely control the IR illumination of a patient's eye 38 and, moreover, to achieve levels of 0, 50 and 100% illumination, if desired. Again, this desired arrangement applies equally to pupilometers 300 and 400. The only difference with pupilometers 300 and 400 is that they do not have yellow LEDS 26, but instead have white LEDS, which are not shown in FIGS. 10 and 13, but which are disposed around objective lenses 316 and 416 in the same manner as yellow LEDS 26 are disposed around objective lens 16.

The blue LEDs are used for ocular illumination in situations where the sclera/iris border of a patient's eye 38 may be difficult to detect with IR illumination alone. As shown in FIG. 4, the blue LED 28 preferably is placed on the same radial arc that is defined by the IR LEDs 24, which surround the objective lens 16. The blue LED 28, when activated by the microprocessor (not shown), preferably emits light having a wavelength of substantially 470 nm. The same is true for the blue LEDS associated with pupilometers 300 and 400. Thus, blue LEDS 328 are preferably placed on the same radial arc that is defined by the IR LEDS 324, which surround the objective lens 316. Blue LEDS 328 also emit light having a wavelength of substantially 470 nm. And the blue LEDS associated with pupilometer 400 (not shown) also emit a light having a wavelength of substantially 470 nm, and are also preferably placed in an arc that is defined by the IR LEDS 424, which surround objective lens 416.

It has been discovered by the inventors hereof that light in the blue color band may be used to substantially improve sclera/iris border image contrast because the iris 37 and sclera 41 of a subject's eye 38 generally have substantially different light absorption and reflection characteristics in the blue color band. Thus, the use of a blue LED for sclera/iris border imaging is believed to be a particularly innovative aspect of the present invention.

Because the human eye is responsive to blue radiation, the blue LEDs preferably are only activated for brief periods of time in relation to the temporal response of a subject's eye 38 or, alternatively, is used in conjunction with the stimulus LEDs 26 (not shown with pupilometers 300 and 400) described below. Moreover, in a preferred form, IR and blue light illumination of the eye 38 of a subject may be performed in a multiplexed fashion, such that the eye of the subject is illuminated with IR light for a first period of time and, thereafter, illuminated with blue light for a second period of time. This is discussed more fully below with reference to FIG. 6.

The microprocessor (not shown) provided on the main signal processing board 34 controls the operation and function of the various components comprising the illumination system as described more fully below.

4. The Stimulus System

The stimulus system of the pupilometer 10 comprises two yellow LEDs 26 and a second beam splitter 20. The yellow LEDs 26 preferably are coupled to the flex circuit 33 and, when activated by the microprocessor (not shown), emit light having a wavelength of substantially 570 nm. Like the first beam splitter 18, the second beam splitter 20 preferably comprises a glass substrate having a thickness of 1.6 mm and is coated with a multi-layer dielectric coating (not shown) to form a wavelength selective filter. The subject side 50 of the beam splitter 20 is coated to enhance reflection at the yellow wavelength band with a 45° angle of incidence, and the user side 52 of the beam splitter 20 is AR coated to minimize effects resulting from multiple reflections in the user's observation path. The stimulus system of the pupilometer 10 preferably provides on-axis illumination of the pupil 43 of the eye 38 of a patient, as shown in FIG. 1.

The stimulus system of pupilometer 300 can comprise yellow LEDS as in pupilometer 10, or white LEDS (not shown). These yellow or white LEDS operate in the same manner as those in pupilometer 10. Additionally, however, pupilometer 300 includes a lenslet array 330, and a diode array 340, which add an additional stimulus function. The diode array 340 functions in the detection of glaucoma by providing blue light from series N concentrated (optically) blue LEDS 320, which can be imaged onto the retina in such a way as to stimulate N specific regions of the retina. The lenslet array 330 focuses the light through the beam splitter 318 appropriately so that the blue light that is emitted reaches a known area of the retina. Furthermore, the diode array 340 has a diffuse yellow light emitting surface 310 to bias the background as yellow against the blue flicker sources 320.

The stimulus system of pupilometer 400 can also comprise yellow LEDS as in pupilometer 10, but more preferably comprises white LEDS (not shown). In pupilometer 400, there are four white LEDS that are placed symmetrically among the IR LEDS 424. Thus, a total of eight LEDS are placed around the objective lens 416 on a common radial displacement from the optical axis of the objective lens 416.

B. Software Components of a Pupilometer in Accordance with the Present Invention The following description of the software applies to pupilometers 10, 300, and 400, but will only be described in connection with pupilometer 10 for convenience and brevity. It should be understood, however, that the software and microprocessor components described herein are designed for use with each of the pupilometers disclosed herein.

Figure 5:
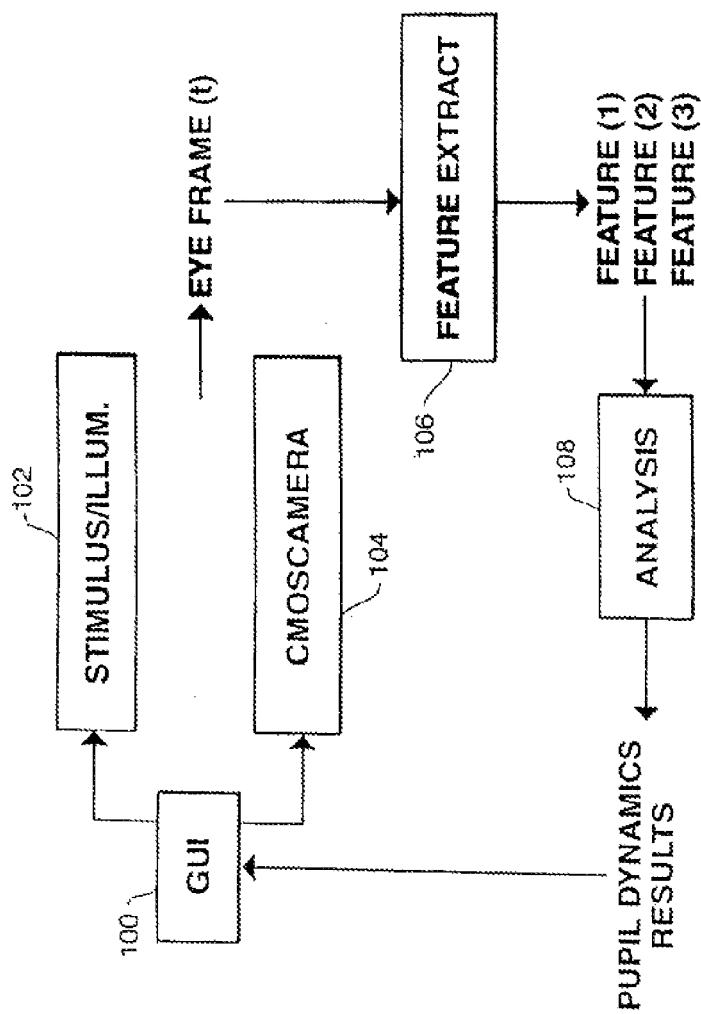
FIG. 5 is a block diagram illustrating a group of programming objects that preferably comprise an operating program of a pupilometer in accordance with the present invention.
Figure 6:
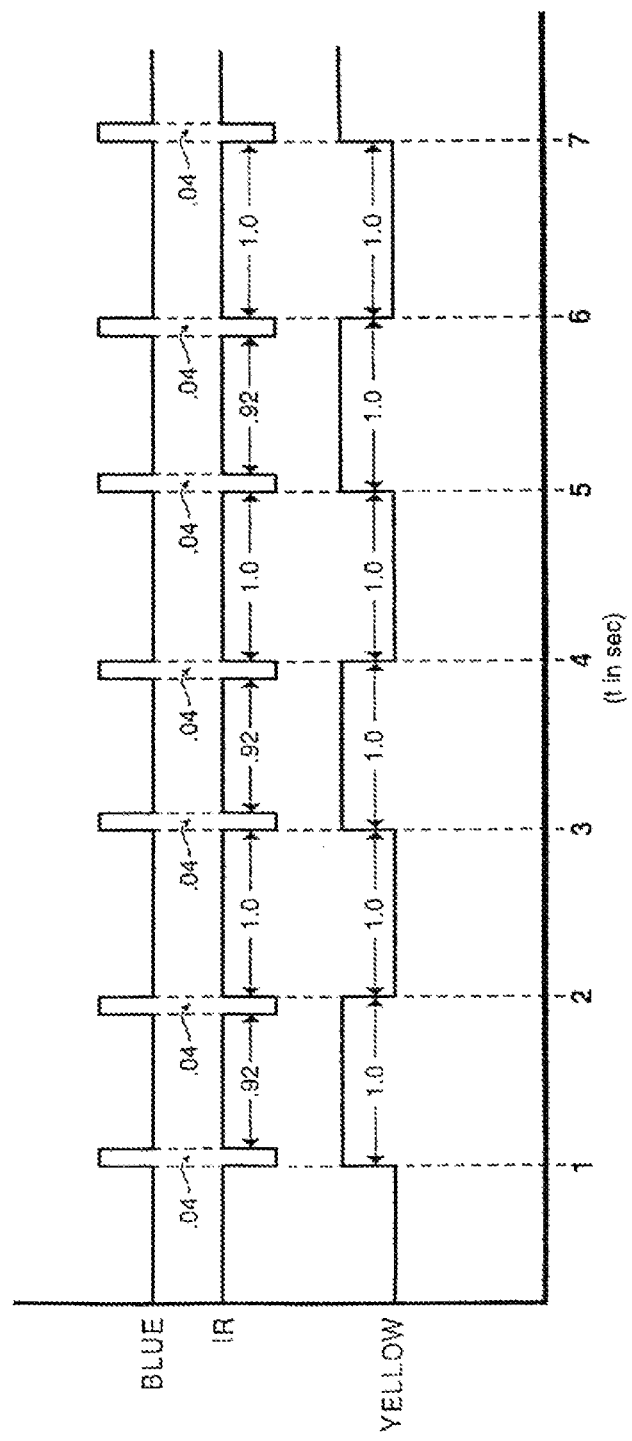
FIG. 6 is a timing diagram illustrating a typical stimulus/illumination sequence for the IR, blue and yellow LEDs that may be used within a pupilometer in accordance with the present invention.

Turning now to FIGS. 5-7, a pupilometer 10 in accordance with the present invention is a microprocessor based system and, therefore, preferably includes several software components or modules for controlling its operation. As is well known in the art, an operating system provides fundamental machine level interfaces between the hardware elements comprising the pupilometer 10. More specifically, various device drivers are used to provide an interface between the microprocessor (not shown) and the imaging sensor 14, IR LEDs 24, yellow LEDs 26, blue LED 28, keypad 39 and liquid crystal display 36.

The highest level of programming or code used within the pupilometer 10 is referred to herein as the P-Program, and the P-Program preferably is divided into five principal objects corresponding to different hardware and mathematical components. The five principal objects are illustrated in block diagram form in FIG. 5 and preferably include a graphic user interface (GUI) object 100, a stimulus/illumination object 102, a CMOS camera object 104, a feature extraction object 106 and an analysis object 108. All of the above-listed objects preferably are developed in Microsoft Visual C++ and Windows CE, and the graphic user interface (GUI) object 100 preferably is based on Win32 Api functions that are available in Windows CE. Visual C++ and Windows CE are software products distributed by Microsoft Corp. of Redmond, Wash.

1. Graphic User Interface (GUI) Object

The graphic user interface object 100 allows for data/information exchange between a user and the pupilometer 10. Information relating to the current status of the pupilometer 10 including mode of operation (i.e., direct or consensual response, left or right eye measurement etc.) and the battery level is displayed via the graphic user interface object 100. All inputs and outputs of the pupilometer 10 preferably are coordinated via the graphic user interface object 100. Verification of subject ID numbers and/or patient identification data may be accomplished under control of the graphic user interface object 100. Measurement parameters are determined and set with the assistance of the graphic user interface object 100. Instructions during measurement sequences and images of the iris 37 of the eye 38 of a subject are provided on the liquid crystal display 36 under control of the graphic user interface object 100. Similarly, results of measurement sequences are displayed on the liquid crystal display 36 under control of the graphic user interface object 100, and the option to transfer measurement results to a printer or network computer (not shown) is available through the graphic user interface object 100.

2. Stimulus/Illumination Object

The stimulus/illumination object 102 defines and controls the function of the yellow LEDs 26, IR LEDs 24 and blue LED 28 and, therefore, controls the stimulation and illumination of the eye 38 of a subject. The stimulus/illumination object 102 defines the various light profiles (i.e., yellow, IR and blue) as a function of time and controls activation of the yellow, IR and blue LEDs 26, 24 and 28, accordingly. In a typical stimulus/illumination sequence, the LEDs 26, 24 and 28 preferably are activated in the manner described below. However, those skilled in the art will appreciate that the stimulus/illumination sequence may be varied depending upon the circumstances of any given situation, and that variations in the stimulus/illumination sequence may be effected through the user interface object 100.

During a typical stimulus/illumination sequence, the LEDs 24, 26 and 28 may be operated as shown in FIG. 6. For example, during a typical measurement sequence, the yellow LEDs 26 may be activated and deactivated for successive 1 second intervals (i.e., "on" for 1 second and "off" for 1 second) for a period of 10 seconds total. Simultaneously, the IR LEDs 24 may be activated for all periods when the yellow LEDs 26 are "off," and may be deactivated, activated and deactivated (i.e., turned "off," "on" and "off") for respective 0.04, 0.92 and 0.04 second intervals, while the yellow LEDs 26 are turned "on." Similarly, the blue LED 28 may be activated, deactivated and activated for respective 0.04, 0.92 and 0.04 second intervals, while the yellow LEDs 26 are turned "on," and may be deactivated during all periods when the yellow LEDs are turned "off." This allows for the operation of the IR LEDs 24 and blue LED 28 to be multiplexed. In such an embodiment, the image frame transfer rate preferably would be set, for example, to 50 frames per second.

3. The CMOS Camera Object

The CMOS camera object 104 controls the transfer of image data frames between the CMOS imaging sensor 14 and memory associated with the microprocessor (not shown) provided on the main signal processing board 34 (i.e., between the imaging sensor 14 and the P-Program). Preferably, the rate of image frame transfer between the imaging sensor 14 and the memory associated with the microprocessor (not shown) may be programmably set within a range from 1 frame per second to 50 frames per second, depending upon the needs and/or desires of the user. However, those skilled in the art will appreciate that in some instances it may be desirable to provide for faster frame transfer rates, and that such rates might be as high or higher than 100 frames per second.

The image frame acquisition or transfer rate is defined by the user under control of the graphic user interface object 100.

4. The Feature Extraction Object

The feature extraction object 106 defines several image processing procedures that are used to isolate a pupil within an image and to extract several pupil features such as size, shape and position from each pupil image data frame. All processing procedures defined by the feature extraction object preferably are performed on each image data frame, with the exception of the automatic thresholding procedure described below. The automatic thresholding procedure is applied during an initial calibration phase and, therefore, does not need to be applied to each image data frame. Rather, the results of the automatic thresholding procedure are used during feature extraction processing for each image data frame. The results of the automatic thresholding procedure also may be used to set and/or adjust image exposure gain settings within the system.

The feature extraction object 106 employs a flying spot processing algorithm to identify the center of the pupil, a fitted circumference and/or radius of the pupil and, preferably, 48 radii representing the distance between the center and perimeter of the pupil at 48 separate angles in an R,θ coordinate system, where θ defines an angular orientation about the center of the pupil, and R represents the radius of the pupil at that orientation. The fitted radius of the pupil is determined by selecting a circumference that best fits a contour of the pupil and by solving the equation 2πr to obtain the radius value (r).

Those skilled in the art will appreciate that, by defining and evaluating 48 distinct radii about the center of the pupil, it is possible in accordance with the present invention to detect one or more non-uniformities or irregularities that may exist around the perimeter of the pupil. It also is possible to characterize the shape of the pupil as circular, elliptical etc. based upon the determined radii. It also is possible to evaluate selected sections of a pupil perimeter to determine whether or not those sections exhibit normal contour characteristics and/or normal responses to visual stimulus. It is believed that these capabilities represent significant improvements over conventional pupilometry systems, as these features allow not only for the performance of conventional pupil aperture and response evaluations, but also for the performance of pupil shape and sectional contour evaluations. Thus, where a particular affliction may produce a defined irregularity in pupil shape or defined sectional response to visual stimulus, the affliction may be identified through the use of a pupilometer in accordance with the present invention.

The inputs to, and outputs obtained from, the flying spot algorithm may be defined as follows:

Input Parameters:
Frame=eye image frame generated by the CMOS imaging sensor 14
Threshold=gray level threshold value; any pixel having a gray scale value greater than the threshold value is considered to be part of the pupil.
Output Parameters:
Output=fitted radius and center of pupil, 48 radii.

It is assumed herein that within the gray scale used by the pupilometer 10 the color black will be associated with a high gray scale value, such as 255, and the color white will be associated with a low gray scale value, such as 0. However, those skilled in the art will appreciate that the relative maximum and minimum values could be reversed.

It is believed that the use of flying spot algorithms are well known in the art and, therefore, that the flying spot algorithm need not be described in detail herein. Nonetheless, the basic flying spot procedure may be described as follows. The flying spot procedure starts with a large circumference centered on the image of an eye and iteratively reduces the size of the circumference. In reducing the size of the circumference and adjusting the center location of the circumference, for each iteration the following momentums will be computed:

$$\mu x = 1/N * \sum_{x,y} \text{gray\_level\_sign}(x,y)(x-x0)$$

$$\mu y = 1/N * \sum_{x,y} \text{gray\_level\_sign}(x,y)(y-y0)$$

$$\mu r = 1/N \sum_{x,y} \text{gray\_level\_sign}(x,y)$$

where N represents the number of pixels having coordinates x,y in the circumference contour; gray_level_sign(x,y) is +1, if the gray level value of the pixel (x,y) is greater than the threshold value; gray_level_sign(x,y) is −1, if the gray level value of the pixel (x,y) is less than the threshold value; and x0,y0 are the center coordinates of the circumference.

The x and y coordinates of the circumference center and the radius are updated as follows:

$$x0=x0+\mu x * \text{Gain\_}x$$

$$y0=y0+\mu y * \text{Gain\_}y$$

$$\text{radius}=\text{radius}+\mu r * \text{Gain\_}r.$$

As indicated above, the updating procedure is applied iteratively, each time calculating the momentum and then changing the center and radius of the flying spot, such that the circumference finally converges to a circumference that best fits the contour of the pupil.

Once the fitted radius and center of the pupil are determined, 48 radii representing the distance between the center and perimeter of the pupil at 48 separate angles in an R,θ coordinate system preferably are determined, where θ defines an angular orientation about the center of a pupil, and R represents the radius of the pupil at that orientation. By evaluating the 48 determined radii, it is possible to characterize the overall shape of the pupil and to determine whether or not any sectional non-uniformities or irregularities are present about the perimeter of the pupil. Such processing may be performed either by the feature extraction object 106 or the analysis object 108.

Another principal function performed by the feature extraction object is thresholding. The thresholding function automatically identifies a gray level value that separates the pupil from the background in an image data frame. Moreover, when an appropriate threshold value is determined, all pixels having a gray level value greater than the threshold value are considered to comprise part of the image of the pupil, and all pixels having a gray level value less than the threshold are considered to correspond to background.

Preferably, the defined threshold value represents the average of a maximum hypothetical threshold value and a minimum hypothetical threshold value. The maximum and minimum hypothetical threshold values are derived through respective histogram analysis routines. Moreover, as shown in FIGS. 7(*a*) and 7(*b*), for each hypothetical threshold value two histograms are evaluated, one for the rows of pixels within an image frame, and one for the columns of pixels within the image frame. The histogram value for a given row or column is determined by counting the pixel locations in that row or column that have a gray level value that exceeds the hypothetical threshold level. Thus, the number of values within a histogram preferably corresponds to the number of rows or columns in the image data frame, and each value represents the number of pixels in the specific row or column that have a gray level exceeding the hypothetical threshold value.

Figure 7B:
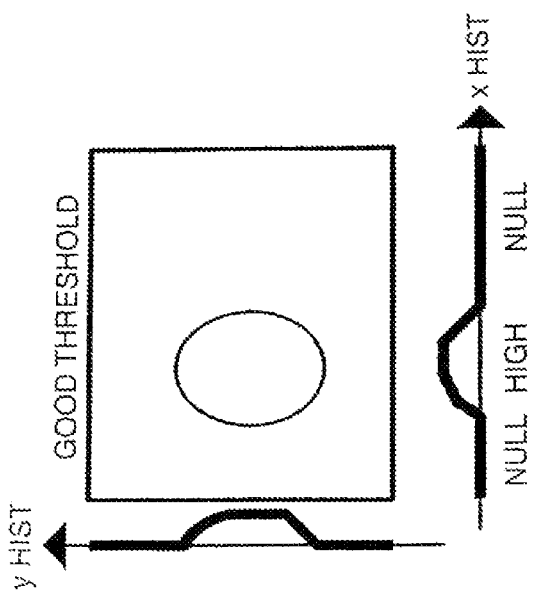
FIGS. 7(a) and 7(b) are illustrations of histogram data sets that may be developed in accordance with a preferred thresholding algorithm utilized by a pupilometer in accordance with the present invention.
Figure 7A:
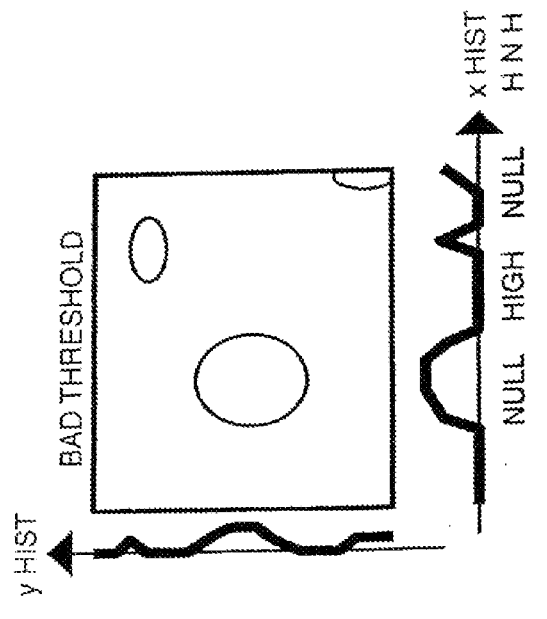

Turning now in particular to FIGS. 7(a) and 7(b) the hypothetical maximum and hypothetical minimum threshold values are determined by iteratively altering a hypothetical threshold value until a prescribed histogram profile is achieved. An acceptable profile is illustrated in FIG. 7(a) and is one in which a null-high-null pattern is achieved for both a row histogram (y Hist) and column histogram (x Hist). More specifically, an acceptable profile preferably comprises a single "high" bordered by a pair of "nulls." Unacceptable profiles are illustrated, for example, in FIG. 7(b).

The hypothetical maximum threshold value is determined by selecting an absolute maximum value and iteratively decreasing that value and deriving corresponding histogram data sets until acceptable row and column histogram profiles are achieved. Similarly, the hypothetical minimum threshold value is determined by selecting an absolute minimum value and iteratively increasing that value and deriving corresponding histogram data sets until acceptable row and column histogram profiles are achieved. Once the hypothetical maximum and minimum threshold values are determined, those values are averaged to determine the defined threshold value that will be used by the feature extraction object 106. Those skilled in the art will appreciate that the defined threshold value may correspond to the maximum hypothetical threshold value, the minimum hypothetical threshold value, or any value that is between those values. Thus, in alternative embodiments, the defined threshold value could be determined, for example, based on a weighted average of the maximum and minimum hypothetical threshold values. In such an embodiment, the defined threshold value may comprise a value corresponding to the sum of the minimum hypothetical threshold value and ⅔ of the difference between the maximum and minimum hypothetical threshold values.

5. The Analysis Object

The analysis object 108 analyzes the configuration characteristics of a pupil as a function of time. Preferably, the analysis object 108 receives, as inputs, from the feature extraction object 106 a plurality of data sets for each captured image data frame. The data sets preferably include the time of image capture in msec, x and y coordinates of the pupil center, radius of the flying spot circumference, 48 radii representing the distance between the center and border of the pupil for 48 selected angles within an R,θ coordinate system, and an applied stimulus record for the relevant entry. Upon receiving the input data sets, the analysis object 108 preferably derives at least the following information from the data sets: minimum pupil aperture, maximum pupil aperture, difference between maximum and minimum pupil apertures, latency of pupil response to yellow light stimulus, pupil constriction velocity, first and second pupil dilation velocities and, if desired, pupil irregularity magnitude and location information. Where pupil irregularities are detected, the location of the irregularity preferably is identified by its θ coordinate. However, graphical indications also may be provided on the display 36 of the pupilometer 10.

Further, in alternative embodiments, the analysis object 108 may include programming for effecting a multi-varied analysis wherein a plurality of selected variables including, for example, latency indicia, constriction velocity indicia, first and second dilation velocity indicia, segmental static and/or dynamic analysis indicia, constriction/dilation velocity ratio indicia, and maximum and minimum diameter indicia are evaluated for one or both eyes of a patient to arrive at one or more scalar values that are indicative of an overall physiologic or pathologic condition of the patient or, alternatively, to arrive at one or more scalar values that are indicative of an overall opto-neurologic condition of the patient.

With regard to the information derived by the analysis object 108, the maximum pupil aperture, minimum pupil aperture and difference determinations require the identification of the maximum pupil aperture and minimum pupil aperture within a set of image data frames and, thereafter, computation of the difference between those values. The latency determination provides an indication in milliseconds of the time that it takes for a pupil to begin to respond to a visible (i.e., yellow) light stimulus pulse. Further, those skilled in the art will appreciate that, when a pupil is exposed to a visual light stimulus pulse, the pupil generally will, after some latency period, constrict and, once the stimulus is discontinued, dilate and return to its original size and configuration. Thus, the analysis object 108 evaluates the response of a pupil to a visual stimulus to determine a pupil constriction velocity and evaluates the response of the pupil to termination of the stimulus to determine first and second dilation velocities. First and second dilation velocities are evaluated because a pupil generally will dilate quickly for a first period of time and, thereafter, will dilate more slowly until its original size and configuration are achieved. Finally, as explained above, an analysis object 108 in accordance with the present invention also preferably identifies any irregularities in the shape of the pupil. Such irregularities may be either static or dynamic in nature. For example, a static irregularity may take the form of an irregular pupil shape in ambient light, whereas a dynamic irregularity may take the form of increased latency for a particular section of the pupil during a response to a the initiation or termination of a visual stimulus. With regard to static irregularities, such irregularities may be identified by identifying the angular orientations of radii that do not fall within prescribed limits, differ from other calculated radii by a predetermined deviation or differ from the fitted radius by a predetermined amount, deviation or percentage.

Finally, an analysis object 108 in accordance with the present invention preferably includes programming for identifying statistical anomalies within derived results. This allows an analysis object 108 in accordance with the present invention to discard either actual pupilary response data sets (i.e., fitted radius, center and radii calculations) or derived data sets (i.e., max aperture, min aperture, latency, constriction rate or dilation rates) when a selected value differs from other values by a statistically significant degree. When such anomalies are identified, the relevant data sets are not included in averaging functions, and where many anomalies are identified, an imaging sequence will be invalidated and must be repeated.

C. Operation of a Pupilometer in Accordance with the Present Invention

The following description of the operation of a pupilometer of the present invention applies to each of pupilometers 10, 300, and 400, but will only be described in connection with pupilometer 10 for convenience and brevity. It should be understood, however, that the software and microprocessor components of each of pupilometers 10, 300, and 400 can be the same, and therefore, the operation of each of these pupilometers can be the same.

Figure 8A:
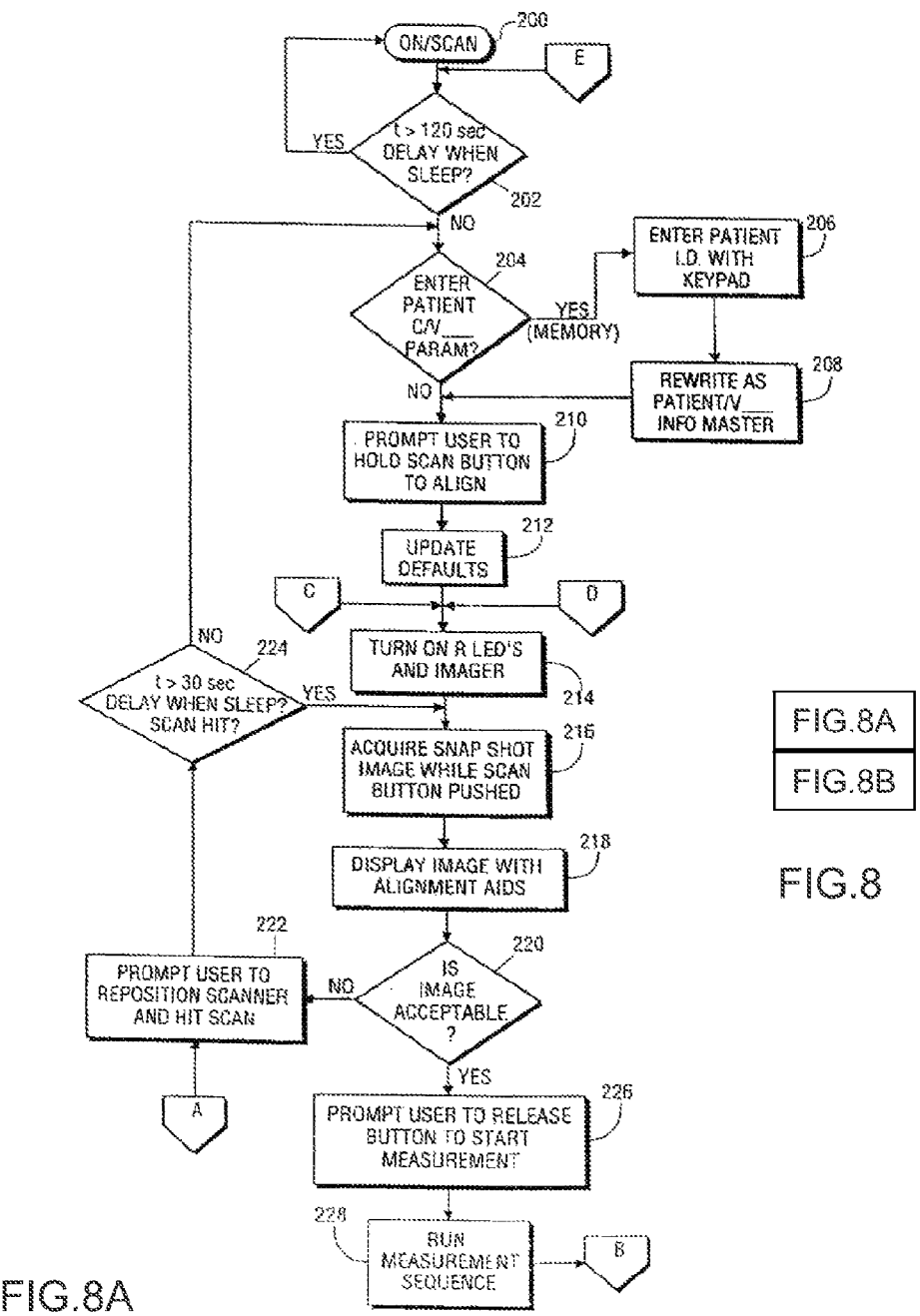
FIG. 8 is a flow chart illustrating a basic operating protocol for a pupilometer in accordance with the present invention.
Figure 8B:
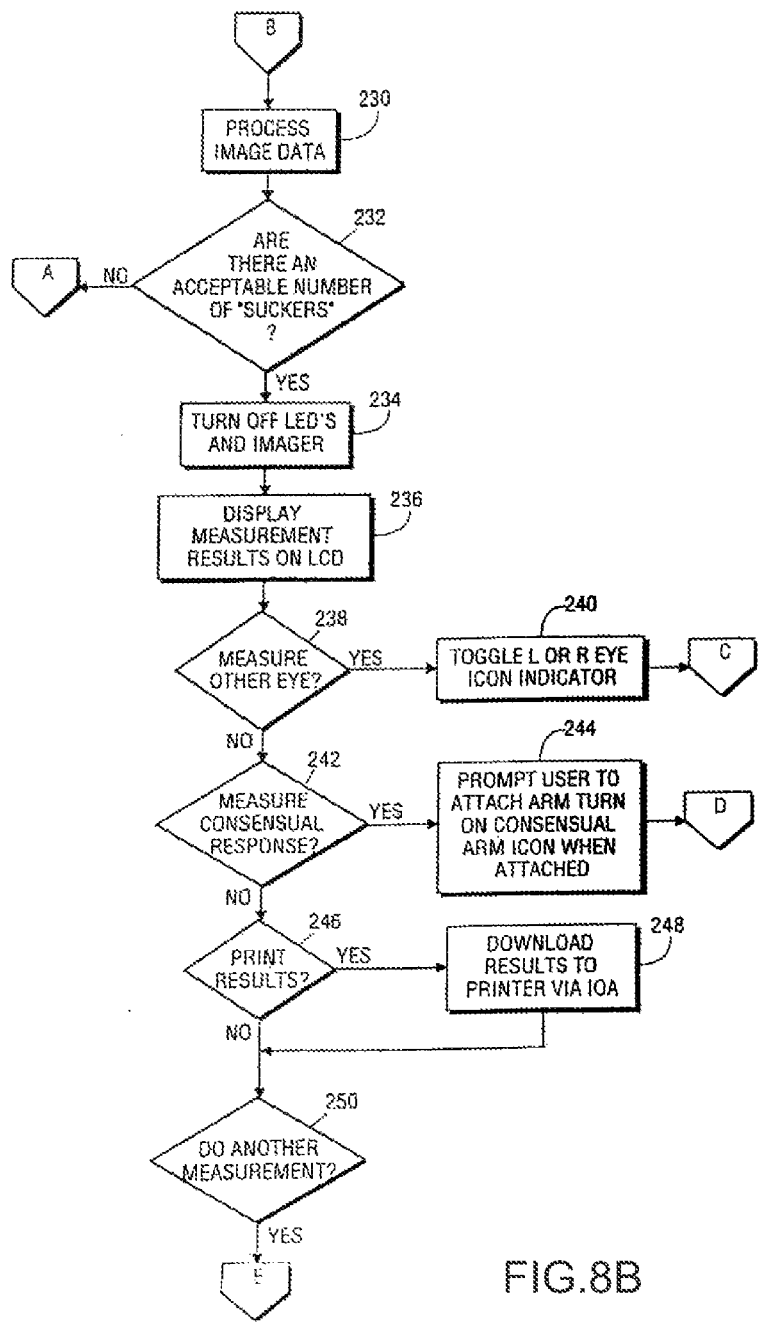

Turning now to FIG. 8, operation of a pupilometer 10 in accordance with the present invention proceeds as follows. Generally the pupilometer 10 will be configured according to a default mode of operation. The default mode defines a set of values for basic operation of the device. The defined values may include, for example, values for scan duration, illumination duration and/or profile, stimulus duration and/or profile and stimulus intensity level. However, it will be appreciated that all of the above-listed values may be programmably set under control of the graphic user interface object 100. Thus, it will be appreciated that default programming values generally will be utilized by the pupilometer 10 absent entry of an override by the user in a scan sequence program mode.

A typical image acquisition and analysis procedure may proceed as follows. If the pupilometer 10 has been idle for a predetermined period of time (e.g., 120 seconds), the pupilometer 10 is automatically placed in a battery-conserving sleep mode (step 202). By depressing the "scan" button 45 (shown in FIG. 2), the user causes the pupilometer 10 to enter a "ready" mode (step 200). At this time, the user is prompted to enter an alphanumeric subject or patient identification number via the keypad 39 or to download any necessary patient information from a network computer via an infrared data interface, such as an IrDA interface that is provided on numerous conventional personal computer products (step 204). Once any requisite patient identification data has been entered into the system, the user is prompted via the liquid crystal display 36 or an audio prompt to hold down the "scan" button 45 and to position the pupilometer 10 in front of the eye 38 of a subject (step 210).

When the user depresses the "scan" button 45, the microprocessor (not shown) initiates an imaging test sequence. The yellow LEDs 26 preferably are not activated during the test sequence. During the test sequence the images that are acquired by the imaging sensor 14 may be displayed on the liquid crystal display (LCD) 36. Preferably, the P-program analyzes the image data frames that are acquired during the test sequence, determines whether or not the pupilometer 10 is properly positioned for obtaining measurements, and determines if all necessary parameters are met to ensure high-quality data recovery. If the test criteria are not met, the user is prompted to reposition the pupilometer 10. After any requisite test criteria are met, the P-program will continue to run the test sequence until the "scan" button 45 is released.

Once the scan button 45 is released, the P-program preferably will initiate a prescribed measurement sequence and will activate the illumination system of the pupilometer 10 as needed during the measurement sequence. Upon completion of the measurement sequence, the user is informed via the LCD 36 or an audio prompt that the measurement sequence has been completed (steps 226-228).

Following completion of the measurement sequence, the P-program preferably will analyze the image data frames that have been obtained and will display the results of the analysis on the LCD 36. If the results are satisfactory (i.e., are statistically sound), the user may then be prompted to download the results to a printer or related network via the IrDA interface (not shown) (step 246). If the results are not satisfactory, the user is prompted to repeat the measurement sequence (step 222).

Finally, after an initial set of measurement are obtained, the user may be prompted for a decision to measure the pupilary characteristics of the other eye of the subject/patient, or the user may be prompted for a decision to make a consensual response measurement (steps 238, 242). The consensual response measurement may take the form of a "swinging flashlight" measurement discussed more fully below. If a consensual measurement is to be performed, the user may be prompted to couple a consensual measurement attachment (shown in FIG. 9) to the pupilometer and to position a yellow LED 52 mounted on the attachment in front of the appropriate eye of the subject/patient. If the consensual measurement attachment is permanently affixed to the pupilometer 10, the user may only need to deploy and/or properly position the attachment.

D. Incorporation of Consensual Measurement Apparatus in a Pupilometer in Accordance with the Present Invention The following description of incorporated consensual measurement apparatus applies to pupilometers 10, 300, and 400, but will only be described in connection with pupilometer 10 for convenience and brevity. It should be understood, however, that each of pupilometers 10, 300, and 400 are hand-held devices having similar dimensions, and the consensual measurement apparatus described herein can be used with each of them.

Figure 9:
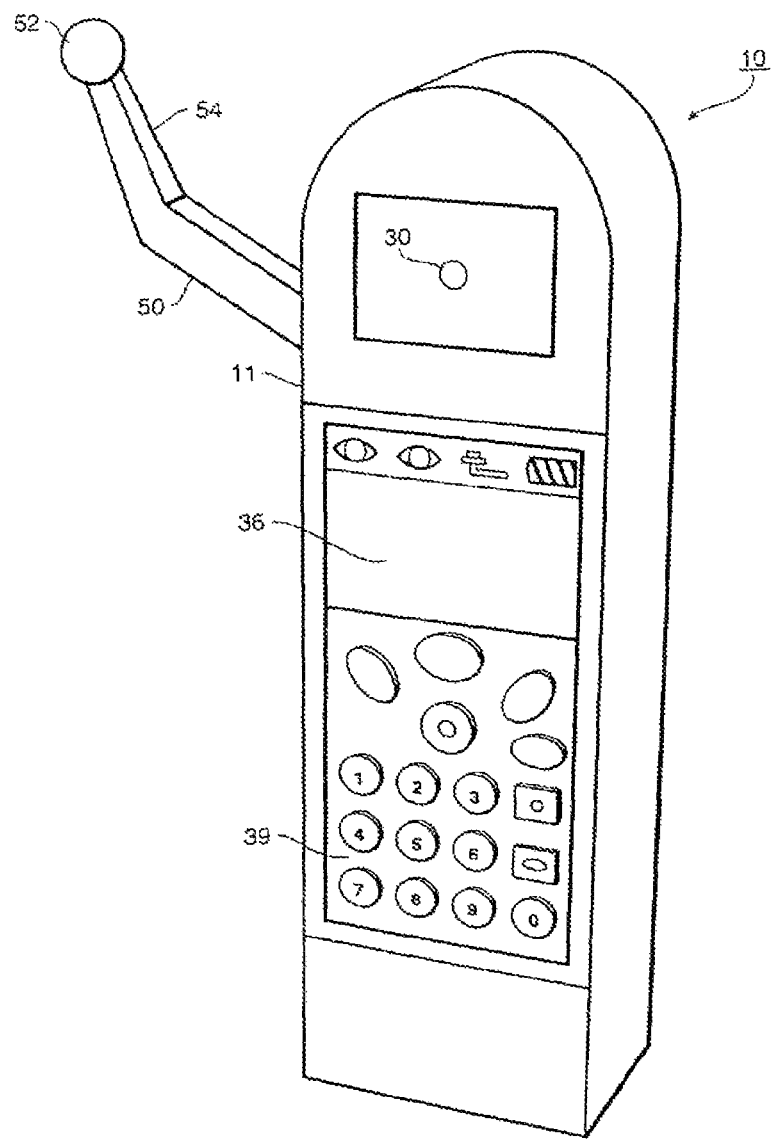
FIG. 9 is an illustration of a pupilometer incorporating a consensual measurement attachment in accordance with the present invention.

Turning now to FIG. 9, a pupilometer 10 in accordance with the present invention may incorporate a consensual measurement apparatus or armature 50 to enable consensual pupilary responses to be analyzed. In a preferred embodiment, the armature 50 may detachably engage a main body 11 of the pupilometer 10. However, as explained above, the armature 50 also may be permanently affixed to the main body 11 of the pupilometer 10.

One test for analyzing consensual pupilary responses is commonly referred to within the medical community as a "swinging flashlight test." During a typical swinging flashlight test one eye of a subject is monitored, and a visible light stimulus is applied first to the eye of the patient that is being monitored, then to the eye of the patient that is not monitored and, finally, again to the eye that is monitored. If the eyes of the patient are normal, the pupil of the monitored eye should constrict in response to all of the light stimulus pulses (regardless of which eye the stimulus pulse is applied to). Following application of the first light stimulus, the pupil of the monitored eye should begin to dilate, and upon application of the second light stimulus (i.e., upon application of stimulus to the non-monitored eye), the pupil of the monitored eye should again constrict. If the monitored pupil does not respond adequately to the second stimulus pulse, it may be inferred that the retina of the non-monitored eye somehow may be impaired. If the monitored pupil does not respond adequately to the third stimulus pulse, it may be inferred that the retina of the monitored eye somehow may be impaired.

By using a consensual measurement attachment 50 in accordance with the present invention, it is possible to perform a "swinging flashlight" test using the pupilometer 10. For example, when performing a "swinging flashlight" test, the P-program may first cause the yellow LEDs 26 within the pupilometer 10 to be activated for a period of, for example, 1 second. The P-program then may deactivate the yellow LEDs 26, and 0.5 second following deactivation of the yellow LEDs 26 may activate for 0.5 second the yellow LED 52 located at the distal end 54 of the consensual attachment. Finally, after deactivating the yellow LED 52 and waiting for a period of, for example, 0.5 second, the P-program may again activate the yellow LEDs 26 for a period of 1 second. Image frames may be obtained by the imaging sensor 14 at a rate of, for example, 10 frames per second and for a total period of 5.0 or more seconds to evaluate the consensual response of the imaged eye. If desired, the process may be repeated a predetermined number of times.

E. Miscellaneous System Calibration and Pupil Identification Processing Techniques The following system calibration and pupil identification processing techniques are applicable to pupilometers 10, 300, and 400, but will only be described in connection with pupilometer 10 for convenience and brevity. It should be understood, however, that just as with the above description of the software, the techniques described now can be used with pupilometers 300 and 400 as well.

In alternative embodiments, the P-program of a pupilometer 10 in accordance with the present invention may incorporate a calibration algorithm that uses acquired data descriptive of the perimeter of the iris 37 of the eye 38 of a patient to define a relationship between pixel spacing data and real world measurement parameters and/or to evaluate an orientation of a patient's eye 38 in relation to the pupilometer 10.

For example, in one innovative aspect, the P-program of a pupilometer 10 may cause the iris of the eye of a patient to be illuminated by blue light (i.e., may activate the blue LED 28) and, while the patient's eye is so illuminated, may obtain an image of the sclera/iris border of the patient's eye. A flying spot or similar processing algorithm may then be used to identify a best fitting elliptical circumference for the sclera/iris border of the patient's eye, and the radii or horizontal and vertical diameters of the circumference may be compared to or correlated with assumed sclera/iris border radii or diameters to provide a correlation between a pixel count and a real world measurement. For example, if the horizontal diameter of a sclera/iris border is assumed to be 11.7 mm, and the sclera/iris border measures 117 pixels in diameter, the P-program of the pupilometer 10 may derive a pixel measurement to real world correlation factor of 10 pixels/mm, and that correlation factor may be used to provide the user with pupil measurement information. In accordance with one preferred form of the present invention, the horizontal diameter of the sclera/iris border is assumed to be 11.75 mm for in all subjects. However, those skilled in the art will appreciate that a different diameter, such as 11.0 mm or 12.0 mm, may also be assumed.

Similarly, by evaluating the shape of the sclera/iris border of an eye it is possible to estimate the angular orientation of the eye with respect to the pupilometer 10 and, moreover, to evaluate the orientation of an eye with relation to a vertical axis of the eye. Preferably, this may be done by evaluating a degree of ellipticity of the imaged sclera/iris border and assuming that the shape of the sclera/iris border has a predetermined elliptical shape. Such, measurements may be further refined by comparing the shape of a pupil to the shape of a surrounding sclera/iris border to determine whether variations in the shape of a pupil arise from angular orientation of the eye in relation to the pupilometer 10, or from non-uniformities or irregularities in the perimeter of the pupil.

In another innovative aspect, a pupilometer 10 in accordance with the present invention may include software for utilizing physical landmarks to assist in locating a pupil within an image data frame. In such an embodiment, the feature extraction object 106 of the P-program executed by the microprocessor (not shown) may include code for identifying characteristic structures of ocular tissue such as eyelids and/or eyelashes within an image data frame, and for using the location of those structures to predict the location of a pupil within the image data frame. Additional landmarks that may be located in accordance with the present invention include the lachrymal punctum, lachrymal caruncula, and lateral and medial papebral commisures of a patient's eye. These landmarks also may be used to identify which eye of a patient is being monitored.

F. Diagnostics Systems and Methods in Accordance with the Present Invention

In still another innovative aspect, the present invention is directed to improved diagnostics systems and methods incorporating a pupilometer 10 and medical database (not shown). For example, it is contemplated in accordance with the present invention that data representative of a plurality of pupilary response or configuration characteristics associated with one or more physical or pathological conditions may be stored within a medical diagnostics data base, that a pupilometer 10 may be used to obtain data descriptive of one or more pupilary response or configuration characteristics from a patient, and that the obtained data may be compared to the stored data within a data analysis system to identify one or more physiologic or pathologic characteristics or conditions of the patient. Further, in a preferred form, the obtained and/or stored pupil configuration data may be descriptive of one or more static or dynamic regional non-uniformities that may exist within the perimeter of a patient's pupil.

Figure 11:
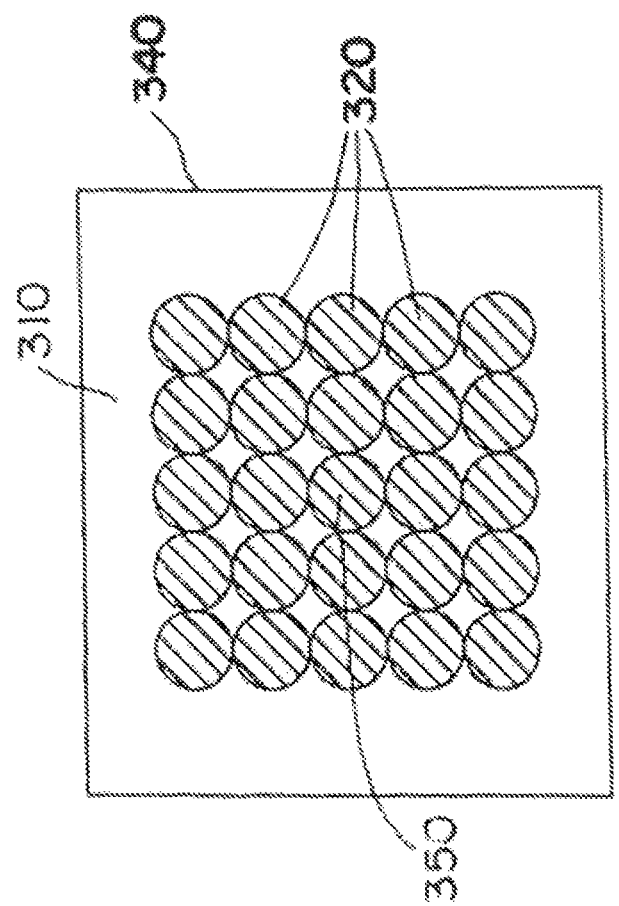
FIG. 11 is a front view of the diode array depicted in FIG. 10.
Figure 12:
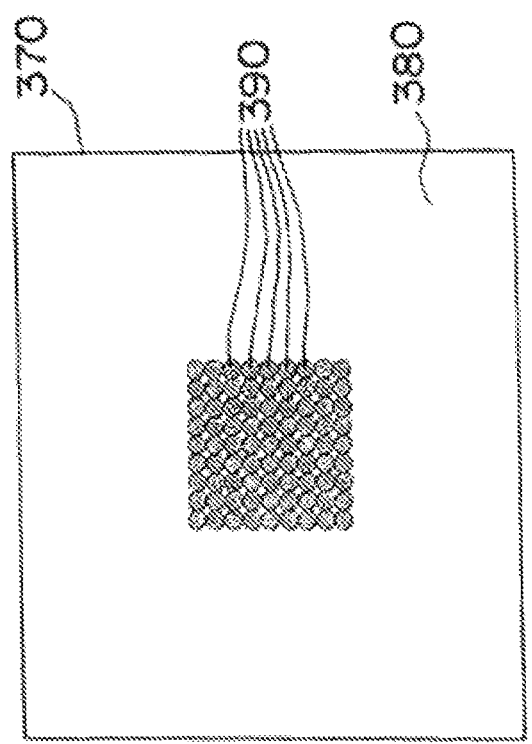
FIG. 12 is a front view of a diode array in accordance with another embodiment of the present invention.

One example is a medical diagnostics system, as shown in FIG. 10, wherein the pupilometer 300 can be used to screen for Glaucoma. The pupilometer 300 can comprise a diode array 340 having a diffuse yellow light emitting surface 310 in conjunction with series N concentrated (optically) blue LEDS 320 which are imaged onto the retina of an eye in such a way as to illuminate N specific regions. A single on-axis red LED 350 can also be used as a fixation target to assure consistent retinal stimulus. The diode array 340 is also shown in FIG. 11 in a two-dimensional frontal or overhead view.

Sensitivity and accuracy of Glaucoma detection are improved by this system and method, which employs the diffuse yellow light emitting surface 310 in order to bias the background as yellow and the N concentrated blue LEDS 320 as flicker sources for stimulating the retina of the eye. Alternatively, the background light can be white while the source of flicker light can generate green light. Again, the IR LEDS are activated to illuminate the eye and enable the imaging sensor to detect pupilary response to the stimluatory light, i.e., the blue or green light.

The microprocessor 34, as shown in FIG. 1, controls the operation and function of this illumination system as previously described. The subject patient's point-of-gaze is verified for each measurement utilizing the tracking features of pupilometer 10. The pupilary response for each of N blue (or green) illumination regions is documented and compared to a database of normal measurements to determine if the response falls out of range. Alternatively, the pupilary response for each of N blue (or green) illumination regions can be compared to a database of measurements that indicate Glaucoma to determine whether they fall within those measurements and therefore indicate Glaucoma. Both amplitude and velocity of pupilary response is detected by the imaging sensor 14 and recorded by the image signal processing board 34. It is expected that in the presence of Glaucoma peripheral retinal response to blue (or green) light stimulus will be compromised.

The pupilometer 10 can also be used to diagnose elevated intracranial pressure. Under conditions of elevated ICP, the profusion of the occulomotor nerve (CNIII) is compromised, therefore affecting the propagation properties of action potentials through nerve fibers. Therefore, under amplitude modulated conditions, which elicit maximal pupilary response, the dynamic properties of the light-reflex as a function of time will deteriorate to a greater extent in those individuals with elevated levels of intracranial pressure. The stimulus/illumination object 102 can be amplitude modulated, and either or both the blue LEDS 28 and the yellow LEDS 26 can act as the stimulus source and can be amplitude modulated also. In this embodiment, the stimulus/illumination object 102 can control the amplitude of the stimulus source to repeatedly cycle the pupil reflex. The pupilometer 10 can be used to capture a sequence of images of the eye while a continuous and amplitude modulated light stimulus is applied to the eye, either by the blue LEDS 28 or the yellow LEDS 26. The P-program software detects the pupil margin and calculates the average rate of change of the pupil as a response to an extended duration amplitude modulated light stimulus source. The average rate of change data is then compared to normative or previously recorded data for the patient or a normal subject as an indicator of abnormality and CNIII involvement due to elevated intracranial pressure.

When the amplitude of the light projected to the eye is increased, the constriction velocity of the pupil should increase. But, the constriction velocity for each successive increase in light stimulus amplitude is generally lower in those individuals who are diagnosed with elevated intracranial pressure. On the other hand, as the amplitude is decreased, dilation velocity in individuals with intracranial pressure increases at a more rapid pace. Thus, constriction and dilation velocity, as well as pupilary amplitude, can be used to determine whether an individual has elevated levels of intracranial pressure.

The pupilometer 10 can also be used to diagnose impairment to brain function. The task of fixating on a target and maintaining this fixation as the target is moved about the visual field requires constant cortical feedback and cerebellar eye movement correction. The ability to visually track a moving target can be assessed by tracking actual point-of-gaze and comparing this information to a stored expected value for a set pattern of target movement. Substantial deviation from the expected value is an indication of brain disorder. Alternatively, the stored expected value can represent brain function impairment rather than representing a normal brain with no brain function impairment. In this case, values that fall within the range of the stored expected value represent brain function impairment. In addition, simultaneous presentation of multiple target points in the visual field has a predictable effect on paint of gaze for normally functioning brains even at a young age. Deviation from the predicted behavior to multiple point targets may give rise to the early diagnosis of Autism.

The system for diagnosing impairment to brain function comprises a pupilometer, such as the pupilometer 300 shown in FIG. 10, a moveable target or light source, a database for storing data descriptive of one or more pupilary characteristics associated with a set pattern of target movement, and a central processing unit coupled to the pupilometer. The target may be on the pupilometer itself, and may be comprised of a light generated by a visible light source, or any other visible object. For example, the pupilometer 300 may have a diode array such as the diode array 370 shown in FIG. 13, which is similar to the diode array 340 used for glaucoma detection. The main difference between the two diode arrays is that the diode array 370 has more LEDS fixed onto a yellow light emitting surface 380 defining a surface area the same or similar in size to the surface area of light emitting surface 310 of diode array 340. Individual elements or LEDS 390 of the diode array 370 can be sequentially turned on and the subjects pupillary movement analyzed according to the subjects ability to track the apparent motion of the LEDS.

The point-of-gaze is determined by detecting features of the eye in addition to the pupil and using fiducial alignment references generated by the system. The P-program will generate a frame by frame history of the point-of-gaze and compare the test results to a figure-of-merit for a normal brain given the same set of visual stimuli. Ultimately the system will indicate the type of tracking error that occurred (i.e., degree of overshoot, magnitude of lag, static dwell time) each of which indicate specific brain disorders.

The pupilometer 10 of FIG. 1 or the pupilometer 400 of FIG. 13 can also be used to test the functional integrity of afferent peripheral and cranial pathways as well as testing efferent cranial nerve involvement in patients with afferent pupilary defects. The pupil is mediated by a complex control system for which the output (pupil size) is determined by the sum of various autonomic inputs. The autonomic inputs that affect the pupil include both sympathetic and parasympathetic constituents. Noxious stimulation such as a pin-prick, sudden exposure to hot or cold, electrical current or pinching should result in a pupilary response. The response may include pupilary amplitude response to pain, reflexive point-of-gaze eye-movement or reflexive blinking.

In the pupilometer testing system described herein, the pupil is observed under a constant background light condition, such as IR light from IR LEDS 24 (or 424 on pupilometer 400), or yellow light from yellow LEDS 26 of the pupilometer 10. Meanwhile, noxious stimulation from a noxious stimulus source 17 is presented to the subject patient, and this stimulation is controlled with precise timing by the pupilometer's microprocessor 34 (or 434 on pupilometer 400), which is in electrical communication with the noxious stimulus source 17 through auxiliary connector 15 (or 415 on pupilometer 400). The magnitude, direction of gaze and temporal characteristics of the eye response including blinking are determined by image processing means in the P-program software. Sources of noxious stimuli, which are controlled by the pupilometer without exposing the patient to tissue damaging effects, include brief pulses of air, release of small bursts of cryogenic spray, such as Halocarbon 134a, and small electrical currents. These stimuli are applied to various dermatopic areas in addition to afferent-sensory areas such as the tympanic membrane and the cornea, which are innervated by cranial nerves.

The noxious stimuli are generated by a noxious stimulus source 17 connected to the pupilometer 10 by auxiliary connector 15 (or auxiliary connector 415 on pupilometer 400). For dorsal root and spinal cord involvement a small canister of compressed $CO_2$ gas with an electronically controlled regulation valve is electrically coupled to the auxiliary connector or output port 15 on the pupilometer 10 (or 415 on pupilometer 400). The valve releases a metered volume of $CO_2$ gas providing a source of extreme cold which can be directed to any dermatome area. The pupil is evaluated for the pain/cold response at progressively lower dermatopic areas until a differential in pupilary response is detected. The P-program software calculates/detects the pupil margin and calculates the gross rate of change of the pupil as a response to the noxious stimulus.

The corneal-blink reflex, which is mediated by afferents of the ophthalmic branch of the trigeminal nerve (CNV) can be tested by the system using compressed air or a fan which produces a small puff of air on the cornea while the P-program monitors pupil as well as eyelid response.

The eye moves away from an ice water stimulus on the tympanic membrane in the ear. A cryogenic spray can produce the same behavior via noxious stimulus to the ear. A $CO_2$ canister and regulated valve as described earlier and electrically coupled to the pupilometer 10 or the pupilometer 400, is used to measure the eye movement in response to this tympanic membrane stimulation.

Finally, the pupilometer 10 or the pupilometer 400 can also be used in connection with a system for testing the functional integrity of auditory pathways (vestibulocochlear nerve and the auditory cortex) by detecting pupilary response to sound stimulus. In this implementation of a pupilometer-based hearing testing system, the pupil is observed under a constant background light condition while an audible stimulus is presented to the subject or patient. This stimulus is controlled with precise timing, amplitude and frequency by the pupilometer's 10 microprocessor 34 (or 340 on pupilometer 400). The amplitude and temporal (i.e., velocity) characteristics of the pupilary response are detected by the imaging sensor 14 (or 414 on pupilometer 400) and recorded by the microprocessor 34 (or 434 on pupilometer 400).

This aspect of the invention can also be implemented by a system comprising a pupilometer as described herein, a sound generating transducer capable of generating sound in various amplitudes and frequencies and in electrical communication with one or more ear-pieces or speakers 19, as shown in FIGS. 1 and 13, a database for storing data descriptive of one or more pupilary characteristics associated with a set pattern of sound stimuli, and a central processing unit. The data stored in the database can represent pupilary responses that are normal and indicative of healthy auditory pathways, or can represent pupilary responses that represent abnormal or disfunctional auditory pathways. In either case, a comparison of the data representing the patient's or subject's pupilary response to the data stored in the database, using the central processing unit, can determine the functional integrity of the patient's auditory pathways.

In another embodiment, an algorithm associated with the memory of microprocessor of the pupilometer, or the memory or microprocessor in communication with the pupilometer, identifies two or three phases that applicant has discovered characterizes a normal or canonical pupil light (or other stimulus) constriction reflex. A canonical reflex is one which is expected from a healthy or normal pupilary reflex response. A healthy or normal pupilary response from a pupil subjected to a stimulus, such as a light stimulus, e.g., a flash of light, or any other stimulus described above, has a period of latency followed by constriction and a period of remaining constricted, followed by dilation back to the original resting dilation.

Stated in more detail, applicant has discovered that the following phases occur immediately subsequent to subjection of the pupil to a stimulus, such as light, or any other stimulus described above. Phase 1 characterizes a latent period following the onset of the light (or other) stimulus (see FIG. 14A). Phase 1 starts at time 0 and has a duration of greater than about 100 msec and less than about 1000 msec. During this latent period the pupil has not yet started constricting and its diameter does not change considerably. The constriction, or phase 2, starts usually only at least 180 or 200 msecs after the onset of the light stimulus and it is characterized by a significant decrease of the pupil diameter. After the constriction, there might be a third phase during which the pupil recovers and tends to return to its initial starting diameter. The pupil diameter during phase 1 is always greater than the pupil diameter during phase 2, and the pupil diameter during phase 2 is always smaller than the pupil diameter during phase 3.

If these two (or three) phases are not identified by the pupilometer, the analyzed pupil profile does not resemble a canonical pupil light reflex. Thus, using the method and system described herein, the pupilometer can determine whether the pupil reflex is characteristic of a canonical pupil light reflex. If not, the pupilometer will provide an output indicating that the pupil reflex is not a canonical pupil light reflex.

Figure 14B:
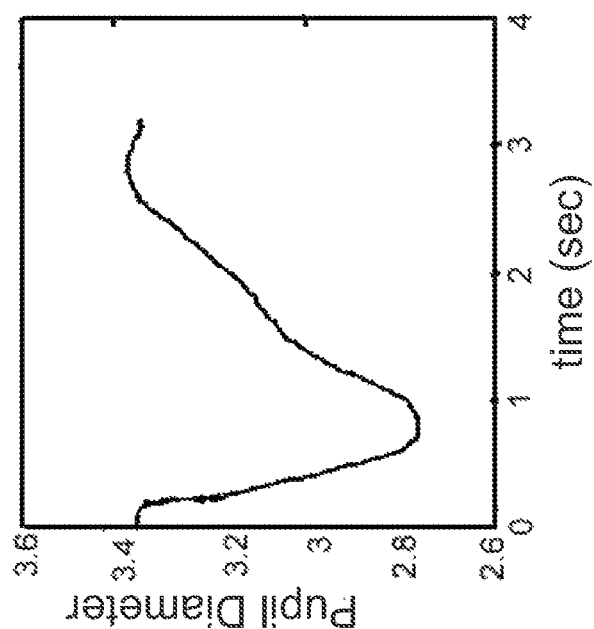
FIGS. 14a-14f are graphical representations identifying the phases characterizing a standard pupil light constriction reflex and a method for screening for a non-responsive or non-canonical pupilary response.
Figure 14A:
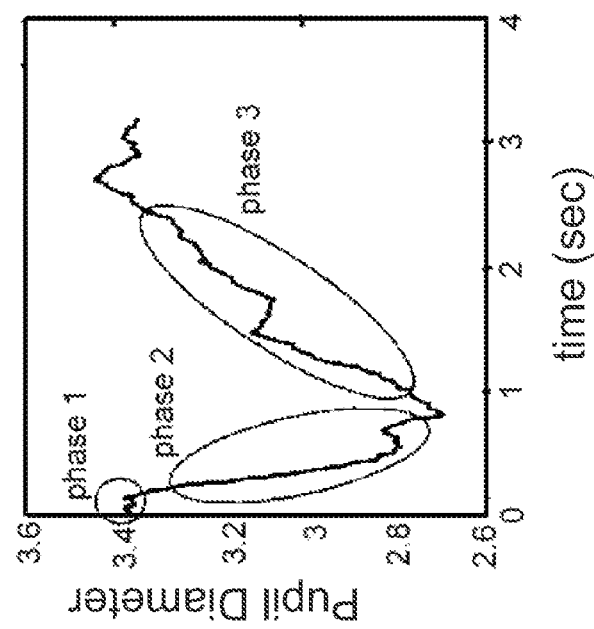
Figure 14D:
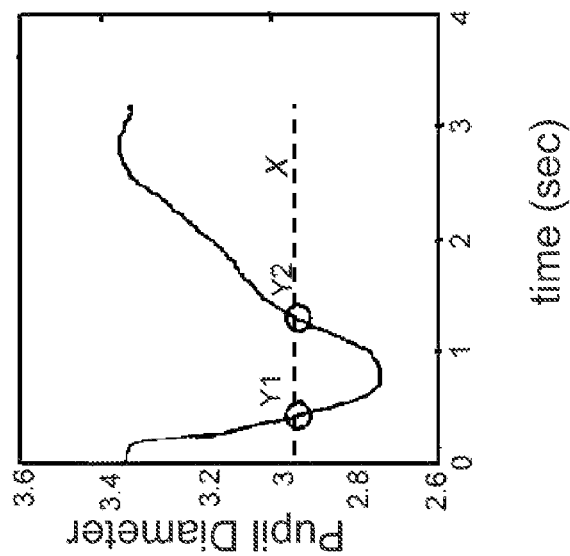
Figure 14C:
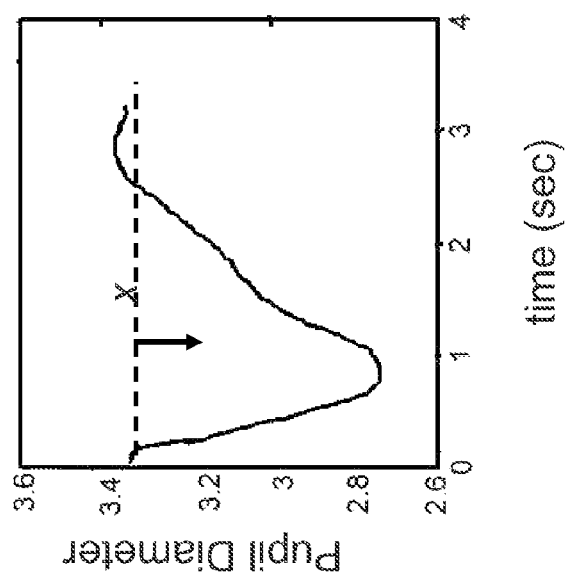

The first step of the algorithm is a low pass noise reduction filtering that removes all the physiological and instrumental noise from the pupil data profile (see the profile in FIG. 14B after the low pass noise reduction operation). Then the algorithm tries different horizontal cuts of the pupil profile; it starts from the very top of the profile (see FIG. 14C) and then goes down step by step with small decrements; for each possible position of the horizontal cut (see dotted line X in FIGS. 14C and 14D) the algorithm tries to validate the following conditions:

a. there is only one (or at most two intersections) between the pupil profile and the horizontal line (see the small circles Y1 and Y2 in FIG. 14D).

b. during phase 1 (before the first intersection, e.g. first circle Y1 in FIG. 14D) the pupil diameter is all above the horizontal line. In other words, immediately subsequent to stimulation of the pupil with a stimulus source, such as light, or any other source described above, the pupil diameter does not increase before it decreases.

c. the duration of phase 1 must be a certain duration of time z. In one embodiment, z is a figure between 260 msec and 1 second. In another embodiment, z is a figure between 100 msec and 1 second. In yet another embodiment, z is a figure between 200 msec and 1 second. In yet another embodiment, z is a figure between 320 msec and 1 second.

d. if there is more than 1 intersection between the pupil profile and the horizontal line, then the duration between the first intersection and the second intersection must be equal to or greater than a duration of time t as measured in milliseconds (msec). In one embodiment, t is 260 msec. In other embodiments, t is 100 msec, 200 msec, 300 msec, 320 msec, 400 msec or greater.

Put another way, the algorithm tries to validate the following conditions:

a. no more than two data points exist representing the same pupil diameter at separate times during duration y, which can be between about 1 and about 4 seconds;

b. a first phase of the pupilary reflex response exists, wherein said first phase is characterized by a period of non-constriction immediately subsequent to time 0 (the onset of stimulus), said first phase having a duration of greater than about 100 msec and less than about 1000 msec;

c. if two data points exist representing the same pupil diameter at two separate times $y^1$ and $y^2$ during duration y, then the duration of time between $y^1$ and $y^2$ is greater than about 100 msec; and d. during the first phase of the pupilary reflex, the diameter of the pupil does not increase before it decreases;

If the algorithm does not find any cut where all of these four conditions are valid, then the algorithm fails and the pupil profile summary or output concludes that the pupil reflex does not resemble a canonical pupil light reflex.

Figure 14F:
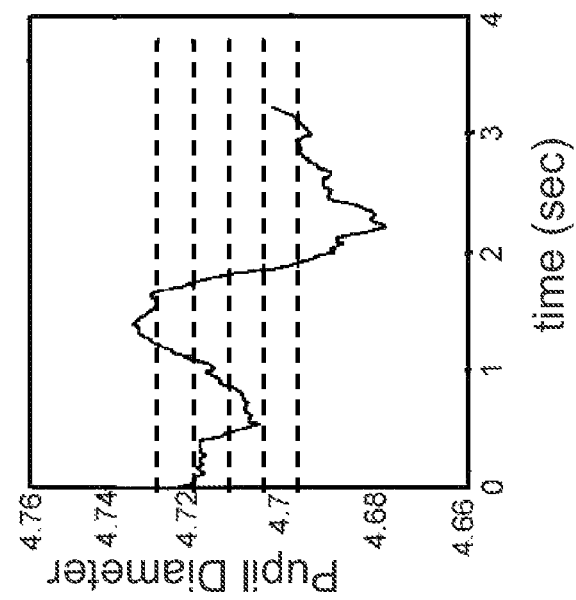
Figure 14E:
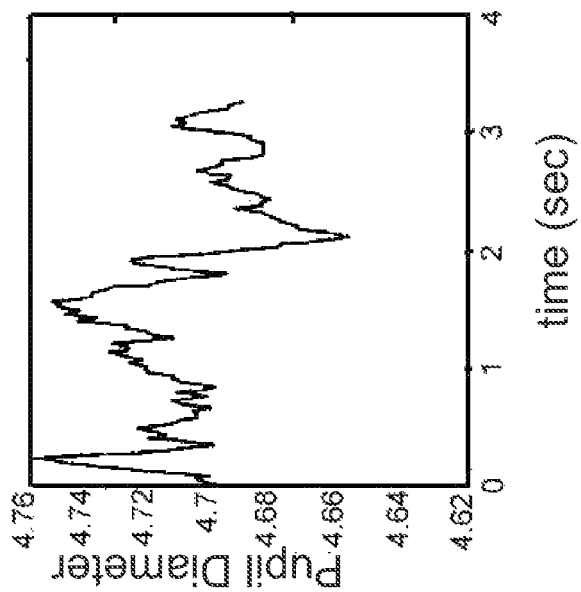

FIGS. 14E and 14F show examples of a non canonical pupil profile according to the present invention. FIG. 14F is the low-passed version of FIG. 14E. In this example, none of the possible horizontal cuts validate the four conditions together. The pupil diameter is measured in millimeters.

The pupilometer can be used to issue the stimulus, or control or modulate it, and it can also be used to image and record the response of the pupil to the stimulus. The graphs shown in FIGS. 14A-14E can be generated by the pupilometer using the algorithm and a low pass filter integrated with the pupilometer or accessed by the pupilometer. Thus, the pupilometer can track the pupil's constriction response over a duration of time starting from a time 0 and lasting for a period of time y. The pupilometer can then collect a plurality of data points, each data point corresponding with a diameter of the pupil at a specific time within the time duration y, and can use those data points to generate a pupil data profile by compiling those data points. The pupilometer can use the above algorithm to then determine whether all of the conditions a through e set forth above are met. The absence or violation of one of the conditions at every cut (see, e.g., x in FIGS. 14C and 14D) indicates that the pupil reflex does not resemble a canonical reflex, and the pupilometer can provide an output or signal that indicates that the pupil reflex does not resemble a canonical pupil reflex. Conversely, if all of the conditions are present, then the pupilometer can provide an output that indicates that the pupil reflex does resemble a canonical pupil reflex.

In another embodiment, the pupilometer can use the above algorithm to determine whether any one of the following conditions are met:
 a. more than two data points exist representing the same pupil diameter at three or more separate times during duration y;
 b. a first phase of the pupilary reflex response exists, wherein said first phase is characterized by a period of non-constriction immediately subsequent to time 0, said first phase having a duration of less than about 100 msec or greater than about 1000 msec;
 c. two data points exist representing the same pupil diameter at two separate times $y^1$ and $y^2$ during duration y, wherein the duration of time between $y^1$ and $y^2$ is less than about 100 msec; or
 d. during the first phase of the pupilary reflex, the diameter of the pupil increases before it decreases.

The existence or presence of at least one of said conditions indicates that the pupil reflex does not resemble a canonical reflex, and the pupilometer can provide an output or signal that indicates that the pupil reflex does not resemble a canonical pupil reflex. Conversely, if none of the conditions are present, then the pupilometer can provide an output that indicates that the pupil reflex does resemble a canonical pupil reflex.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

We claim:

1. A method of screening a pupil of a subject to determine whether the pupil reflex resembles a canonical pupil reflex comprising the steps of:
 stimulating said pupil with a stimulus source;
 using a pupilometer, tracking the pupil's constriction response, wherein the step of tracking the pupil constriction response begins when the pupil is stimulated;
 using the pupilometer, collecting a plurality of data points, each data point corresponding with a diameter of the pupil at a specific point in time while the pupil is stimulated;
 using the pupilometer, generating a pupil data profile by compiling the data points; and
 using the pupilometer, determining whether each of the following conditions is met:
 a. more than two data points exist representing the same pupil diameter at three or more separate points in time during a period of no more than about four seconds in a pupil that is reactive to the stimulus;
 b. a first phase of the pupilary reflex response exists, wherein said first phase is characterized by a period of non-constriction immediately subsequent to stimulating the pupil, said first phase having a duration of less than about 100 msec or greater than about 1000 msec;
 c. two data points exist representing the same pupil diameter at two separate points in time, wherein said two separate points in time are within about 100 msec of each other in a pupil that is reactive to the stimulus; or
 d. during the first phase of the pupilary reflex, the diameter of the pupil increases before it decreases;
  wherein if the pupilometer determines that none of said conditions exists, the pupilometer provides an output that indicates that the pupil reflex resembles a canonical reflex.

2. A method of screening a pupil of a subject to determine whether the pupil reflex resembles a canonical pupil reflex comprising the steps of:
 stimulating said pupil with a stimulus source;
 using a pupilometer, tracking the pupil's constriction response, wherein the step of tracking the pupil constriction response begins when the pupil is stimulated;
 using the pupilometer, collecting a plurality of data points, each data point corresponding with a diameter of the pupil at a specific point in time while the pupil is being stimulated;
 using the pupilometer, generating a pupil data profile by compiling the data points; and
 using the pupilometer, determining whether each of the following conditions is met:
 a. more than two data points exist representing the same pupil diameter at three or more separate points in time during a period of no more than about four seconds in a pupil that is reactive to the stimulus;
 b. a first phase of the pupilary reflex response exists, wherein said first phase is characterized by a period of non-constriction immediately subsequent to stimulating the pupil, said first phase having a duration of less than about 100 msec or greater than about 1000 msec;
 c. two data points exist representing the same pupil diameter at two separate points in time, wherein, said two separate points in time are within about 200 msec of each other in a pupil that is reactive to the stimulus; or
 d. during the first phase of the pupilary reflex, the diameter of the pupil increases before it decreases;
  wherein if the pupilometer determines that none of said conditions exists, the pupilometer provides an output that indicates that the pupil reflex resembles a canonical reflex.

3. A method of screening a pupil of a subject to determine whether the pupil reflex resembles a canonical pupil reflex comprising the steps of:
 stimulating said pupil with a stimulus source;
 using a pupilometer, tracking the pupil's constriction response, wherein the step of tracking the pupil constriction response begins when the pupil is stimulated;
 using the pupilometer, collecting a plurality of data points, each data point corresponding with a diameter of the pupil at a specific point in time while the pupil is being stimulated;
 using the pupilometer, generating a pupil data profile by compiling the data points; and
 using the pupilometer, determining whether each of the following conditions is met:
 a. more than two data points exist representing the same pupil diameter at three or more separate points in time during a period of no more than about four seconds in a pupil that is reactive to the stimulus;
 b. a first phase of the pupilary reflex response exists, wherein said first phase is characterized by a period of non-constriction immediately subsequent to stimulating the pupil, said first phase having a duration of less than about 100 msec or greater than about 1000 msec;
c. two data points exist representing the same pupil diameter at two separate points in time, wherein said two separate points in time are within about 300 msec of each other in a pupil that is reactive to the stimulus; or
d. during the first phase of the pupilary reflex, the diameter of the pupil increases before it decreases;
   wherein if the pupilometer determines that none of said conditions exists, the pupilometer provides an output that indicates that the pupil reflex resembles a canonical reflex.

4. A method of screening a pupil of a subject to determine whether the pupil reflex resembles a canonical pupil reflex comprising the steps of:
   stimulating said pupil with a stimulus source;
   using a pupilometer, tracking the pupil's constriction response, wherein the step of tracking the pupil constriction response begins when the pupil is stimulated;
   using the pupilometer, collecting a plurality of data points, each data point corresponding with a diameter of the pupil at a specific point in time while the pupil is being stimulated;
   using the pupilometer, generating a pupil data profile by compiling the data points; and
   using the pupilometer, determining whether each of the following conditions is met:
a. more than two data points exist representing the same pupil diameter at three or more separate points in time during a period of no more than about four seconds;
b. a first phase of the pupilary reflex response exists, wherein said first phase is characterized by a period of non-constriction immediately subsequent to stimulating the pupil, said first phase having a duration of less than about 100 msec or greater than about 1000 msec;
c. two data points exist representing the same pupil diameter at two separate points in time, wherein said two separate points in time are within about 400 msec of each other in a pupil that is reactive to the stimulus; or
d. during the first phase of the pupilary reflex, the diameter of the pupil increases before it decreases;
   wherein if the pupilometer determines that none of said conditions exists, the pupilometer provides an output that indicates that the pupil reflex resembles a canonical reflex.

5. A method of screening a pupil of a subject to determine whether the pupil reflex resembles a canonical pupil reflex comprising the steps of:
   stimulating said pupil with a stimulus source;
   using a pupilometer, tracking the pupil's constriction response, wherein the step of tracking the pupil constriction response begins when the pupil is stimulated;
   using the pupilometer, collecting a plurality of data points, each data point corresponding with a diameter of the pupil at a specific point in time while the pupil is being stimulated;
   using the pupilometer, generating a pupil data profile by compiling the data points; and
   using the pupilometer, determining whether each of the following conditions is met:
a. more than two data points exist representing the same pupil diameter at three or more separate points in time during a period of no more than about four seconds in a pupil that is reactive to the stimulus;
b. a first phase of the pupilary reflex response exists, wherein said first phase is characterized by a period of non-constriction immediately subsequent to stimulating the pupil, said first phase having a duration of less than about 100 msec or greater than about 1000 msec;
c. two data points exist representing the same pupil diameter at two separate points in time, wherein said two separate points in time are within about 260 msec of each other in a pupil that is reactive to the stimulus; or
d. during the first phase of the pupilary reflex, the diameter of the pupil increases before it decreases;
   wherein if the pupilometer determines that none of said conditions exists, the pupilometer provides an output that indicates that the pupil reflex resembles a canonical reflex.

\* \* \* \* \*